US011124579B2

(12) United States Patent
Teo et al.

(10) Patent No.: US 11,124,579 B2
(45) Date of Patent: Sep. 21, 2021

(54) ANTI OLIGOSACCHARIDE ANTIBODY

(71) Applicants: AGENCY FOR SCIENCE, TECHNOLOGY AND RESEARCH, Singapore (SG); NATIONAL UNIVERSITY OF SINGAPORE, Singapore (SG)

(72) Inventors: Chong Kok Teo, Singapore (SG); Andre Boon Hwa Choo, Singapore (SG); Wee Joo Chng, Singapore (SG)

(73) Assignees: AGENCY FOR SCIENCE, TECHNOLOGY AND RESEARCH, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/498,550

(22) PCT Filed: Mar. 29, 2018

(86) PCT No.: PCT/SG2018/050158
§ 371 (c)(1),
(2) Date: Sep. 27, 2019

(87) PCT Pub. No.: WO2018/182529
PCT Pub. Date: Oct. 4, 2018

(65) Prior Publication Data
US 2020/0024359 A1 Jan. 23, 2020

(30) Foreign Application Priority Data
Mar. 29, 2017 (SG) .......................... 10201702572P

(51) Int. Cl.
*A61K 47/68* (2017.01)
*A61K 47/64* (2017.01)
*C07K 16/28* (2006.01)
*C07K 16/30* (2006.01)
*G01N 33/574* (2006.01)

(52) U.S. Cl.
CPC .......... *C07K 16/3061* (2013.01); *A61K 47/64* (2017.08); *A61K 47/6825* (2017.08); *A61K 47/6851* (2017.08); *C07K 16/2803* (2013.01); *G01N 33/57469* (2013.01); *C07K 2317/24* (2013.01); *C07K 2317/30* (2013.01); *C07K 2317/73* (2013.01); *C07K 2317/77* (2013.01); *G01N 2333/70596* (2013.01)

(58) Field of Classification Search
CPC ............ C07K 16/3061; C07K 16/2803; C07K 2317/24; C07K 2317/30; C07K 2317/73; C07K 2317/77; C07K 16/44; A61K 47/6825; A61K 47/6851; A61K 47/64; A61K 2039/505; A61P 35/00; A61P 35/02; G01N 2800/50; G01N 33/57469; G01N 2333/70596
See application file for complete search history.

(56) References Cited

FOREIGN PATENT DOCUMENTS

| WO | WO-00-29004 A1 | 5/2000 |
| WO | WO-2004/100898 A2 | 11/2004 |
| WO | WO-2008/019378 A1 | 2/2008 |
| WO | WO-2010/051391 A1 | 5/2010 |
| WO | WO-2014/153002 A1 | 9/2014 |
| WO | WO-2016/070089 A2 | 5/2016 |

OTHER PUBLICATIONS

Rudikoff et al., Proc. Natl. Acad. Sci. USA, 1982, 79(6):1979-1983. (Year: 1982).*
Paul, Fundamental Immunology, 3rd Edition, 1993, pp. 292-295. (Year: 1993).*
Colman, Research in Immunology, 1994, 145:33-36 (Year: 1994).*
Vogelstein et al., Nature Medicine, 2004, 10(8): 789-799. (Year: 2004).*
Cancer information from National Institute of Cancer, Apr. 29, 2010, pp. 1-2 (Year: 2010).*
Adjiri A. DNA Mutations May Not Be the Cause of Cancer. Oncol Ther. 2017;5(1):85-101 (Year: 2017).*
Murphy C, Stack E, Krivelo S, Breheny M, Ma H, O'Kennedy R. Enhancing recombinant antibody performance by optimally engineering its format. J Immunol Methods. Dec. 2018;463:127-133. (Year: 2018) (Year: 2018).*
Search Report in International Application No. PCT/SG2018/050158 dated Jun. 7, 2018, 8 pages.
Bouchon et al., "Cutting Edge: Activation of NK Cell-Mediated Cytotoxicity by a SAP-Independent Receptor of the CD2 Family", J. Immunol, vol. 167, No. 10, Nov. 15, 2001, pp. 5517-5521.
Chothia et al., "Conformations of Immunoglobulin Hypervariable Regions", Nature vol. 342, Dec. 1989, pp. 877-883.
Holliger et al., "Engineered Antibody Fragments and the Rise of Single Domains", Nature Biotechnology, vol. 23, No. 9, Sep. 2005, pp. 1126-1136.

(Continued)

*Primary Examiner* — Hong Sang
*Assistant Examiner* — Sung Min Yoon
(74) *Attorney, Agent, or Firm* — Marshall, Gerstein & Borun LLP

(57) ABSTRACT

An antigen-binding protein, or an antigen-binding fragment thereof that binds to a Lewis X type glycan on SLAMF7, comprising (1) a heavy chain variable domain comprising a VHCDR1 having the amino acid sequence GYTFTSYWIH; a VHCDR2 having the amino acid sequence EINPSNGRTNFNEKFKN and a VHCDR3 having the amino acid sequence VDYDEAY; and (ii) a light chain variable domain comprising a VLCDR1 having the amino acid sequence RSSKSLLHSNGITYLY, a VLCDR2 having the amino acid sequence QMSNLAS, and a VLCDR3 having the amino acid sequence AQNLELWT is provided. Methods of using the antibody for detecting or treating cancer, and a kit comprising the antibody are also provided.

16 Claims, 30 Drawing Sheets
Specification includes a Sequence Listing.

(56) References Cited

OTHER PUBLICATIONS

Woo et al., "PDL241, a Novel Humanized Monoclonal Antibody, Reveals CD319 as a Therapeutic Target for Rheumatoid Arthritis", Arthritis Research & Therapy, vol. 15, Dec. 2013, pp. R207:1-15.
Communication Pursuant to Rules 70(2) and 70a(2) EPC in EP Application No. 18777756.0 dated Jan. 19, 2021, 1 page.
Extended European Search Report in EP Application No. 18777756.0 dated Dec. 14, 2020, 7 pages.
Harvey et al., "Elotuzumab Anti-CS1 Monoclonal Antibody Treatment of Multiple Myeloma", Drugs of the Future, vol. 38, No. 7, Jul. 1, 2013, pp. 461-465.
Written Opinion in SG Application No. 11201907923V dated Oct. 29, 2020, 6 pages.
Invitation to Respond to Written Opinion in SG Application No. 11201907923V dated Nov. 3, 2020, 1 page.
Notice of Eligibility for Grant for SG Application No. 11201907923V dated May 19, 2021, 1 page.
Examination Report in SG Application No. 11201907923V dated May 14, 2021, 5 pages.

\* cited by examiner

FIG. 6

| Cell line type | Cell line | % Binding | |
|---|---|---|---|
| | | SLAMF7 | Anti-CD319 |
| t(4;14) Multiple Myeloma | KMS11 | - | + |
| | KMS28/BM | -/+ | +++ |
| | KMS18 | - | +++ |
| | OPM2 | - | +++ |
| Non t(4;14) Multiple Myeloma | MM1.S | - | ++ |
| | OCI-MY5 | - | -/+ |
| | RPMI8226 | - | - |
| Burkitt's Lymphoma | P493 | - | - |
| Acute Myeloid Leukemia | MOLM14 | +++ | -/+ |
| | KG1 | +++ | -/+ |
| | OCI-AML2 | +++ | +++ |
| | OCI-AML3 | +++ | +++ |
| | NB4 | + | + |
| | MV4-11 | ++ | ++ |
| | EOL1 | +++ | -/+ |
| | Mono-Mac1 | +++ | +++ |
| | HL60 | ++ | + |
| | MEG01 | ++ | -/+ |
| | THP1 | + | -/+ |
| | CMK | - | - |
| | HEL | - | - |
| | MGS | - | - |

Legend:
- : <20%
+/- : 20-40%
+ : 40-60%
++ : 60-80%
+++ : >80%

FIG. 7

| Cell line type | Cell line | % Binding |
|---|---|---|
| NSCLC | PC9 | +++ |
| Ovarian | OVCAR3 | +++ |
|  | SKOV3 | + |

Legend:
- −:   <20%
- +/−: 20-40%
- +:   40-60%
- ++:  60-80%
- +++: >80%

FIG. 8

| Cell type | Cell line | % Binding |
|---|---|---|
| Epithelial | MCF10a | - |
|  | HME1 | - |
|  | HEK293 | - |
|  | HPNE | - |
| Endothelial | HUVEC | - |
|  | b4G12 | - |
| Adult MSC | 1 donor | ++ |
| PBMC | 3 donors | ++ |

Legend:
- -: <20%
- +/-: 20-40%
- +: 40-60%
- ++: 60-80%
- +++: >80%

FIG. 9

| | | | | | | | |
|---|---|---|---|---|---|---|---|
| | 786-O<br>Kidney | A2780<br>Ovarian<br>(M, Stem A) | A549<br>Lung<br>(NSCLC) | ACHN<br>Kidney | AGS<br>Gastric<br>Adenocarcinoma | BT549<br>Breast<br>TNBC | BxPC3<br>Pancreas |
| | G1+ | G1+ | G1+ | G1+ | | G1+ | G1+ |
| | Caki-3<br>Lung<br>(NSCLC) | CHL<br>Ovarian<br>(int. M, Stem A) | CL-73<br>Lung<br>(Gefitinib-Resistance) | CMK<br>AML<br>DS-Onco | COLO205<br>Colorectal<br>Metastatic-Ascites | DLD1<br>Colorectal<br>Primary Tumor | H1299<br>Lung<br>(NSCLC) |
| | G1+ | G1+ | | G1+ | G1+ | G1+ | |
| | HaCaT<br>Normal<br>Keratinocytes | HCC827<br>Lung<br>(NSCLC) | HCT116<br>Lung<br>(NSCLC) | HCT15<br>Colorectal<br>Primary Tumor | HEK293<br>Normal<br>Embryonic Kidney | HeLa<br>Cervical | Hep G2<br>Liver |
| | G1+ | G1+ | G1+ | G1+ | G2+ | G2+ | G2+ |
| | HES3<br>Normal<br>Embryonic Stem Cell | HEY<br>Ovarian<br>(int. M) | NH-1<br>Normal<br>Fibroblast | HME-1<br>Normal<br>hTERT-Mammary | Hs578T<br>Breast<br>TNBC | HT-29<br>Colorectal<br>Primary Tumor | HUVEC<br>Normal<br>Vascular Endothelial |
| | not tested | G1+ | G1+ | G1+ | G1+ | G1+ | G1+ |
| | IGROV-1-STI<br>Ovarian<br>(int. M) | IMR90<br>Normal<br>Fibroblast | KMS11<br>MM<br>t(4;14) | KMS18<br>MM<br>t(4;14) | MCF-10A<br>Normal<br>Mammary | MCF7<br>Breast<br>Luminal A | MDA-MB-231<br>Breast<br>TNBC |
| | G1+ | G1+ | G1+ | G1+ | G1+ | | G1+ |
| | MEG-01<br>AML<br>Non-DS Adult | MM.1S<br>MM | Mono-Mac-1<br>AML | NRK5<br>Normal<br>Fibroblast | OVCAR-3<br>Ovarian<br>(E Stem A) | PC-9<br>Lung<br>(NSCLC) | PLC.PRF-5<br>Liver |
| | G1+ | G1+ | | G1+ | | | G1+ |
| | SF-268<br>Brain<br>CNS | SF-295<br>Brain<br>CNS | SK-BR3<br>Breast<br>HER2+ | SK-MEL-2<br>Skin<br>Melanoma | SK-MEL-28<br>Skin<br>Melanoma | SKOV-3<br>Ovarian<br>(int. M) | SKOV-3 SBF<br>Ovarian<br>(CICF treated) |
| | G1+ | G1+ | | G1+ | G1+ | | |
| | SW620<br>Colorectal<br>Metastatic-Lymph Node | T-47D<br>Breast<br>Luminal A | THP-1<br>AML | TK-10<br>Kidney | TM-17<br>Head & Neck | XG-6<br>MM | |
| | | G1+ | G1+ | G1+ | G1+ | G1+ | |

FIG. 10
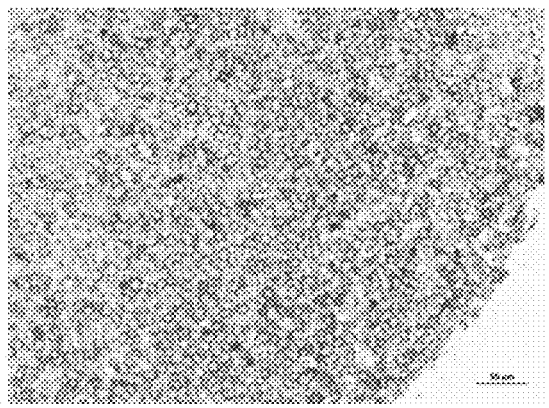 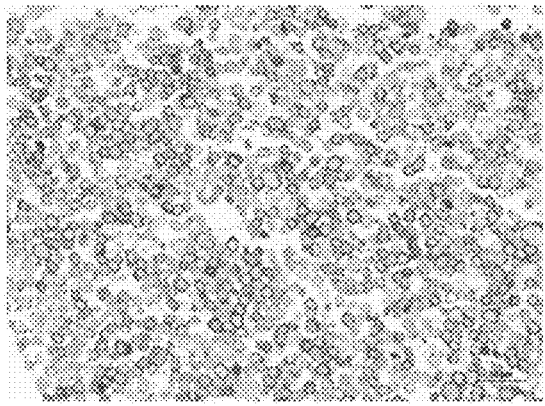
Mono Mac 1 PC9

FIG. 17

| Cell lines | Average Binding % | Relative Cytotoxicity % |
|---|---|---|
| Mono-Mac-1 | 99.7 | 98 |
| MOLM14 | 98.7 | 30 |
| OCI-AML3 | 98.1 | 83 |
| OCI-AML2 | 95 | 79 |
| KG-1 | 92.9 | 46 |
| EOL-1 | 87.5 | 73 |
| MEG-01 | 74.8 | 76 |
| HL60 | 74 | 66 |
| MV4:11 | 65.5 | 70 |
| NB-4 | 55.5 | 51 |
| THP-1 | 47 | 73 |
| HEL | 2 | 6 |
| MG-S | 1.16 | 3 |
| CMK | 0.905 | -14 |

FIG. 21
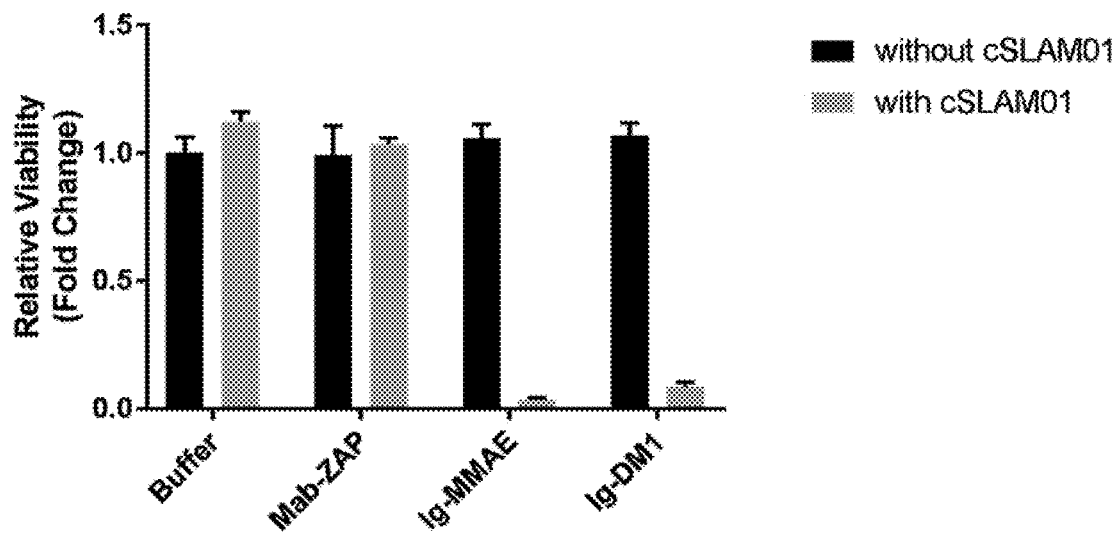
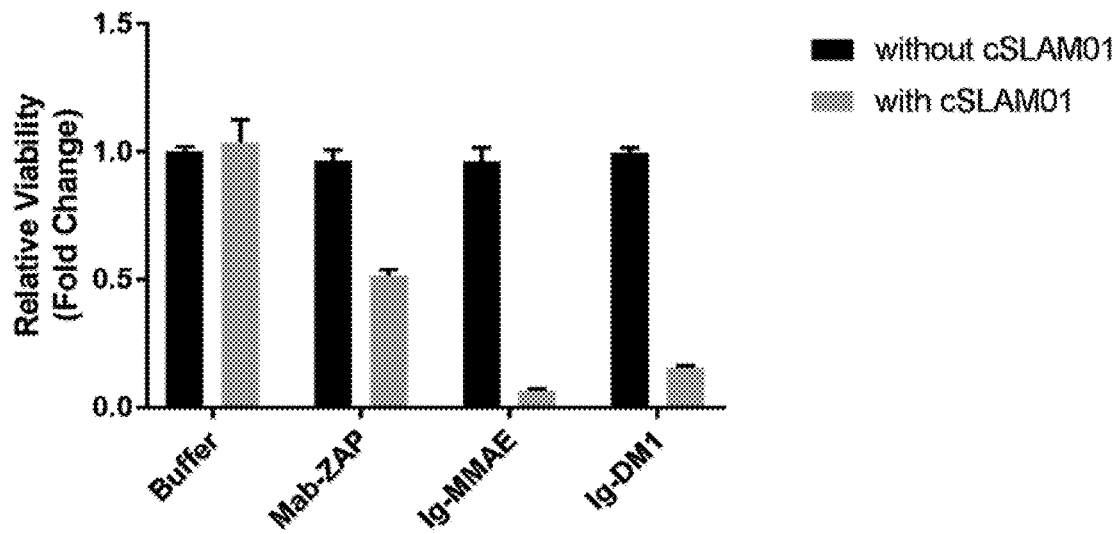

FIG. 28

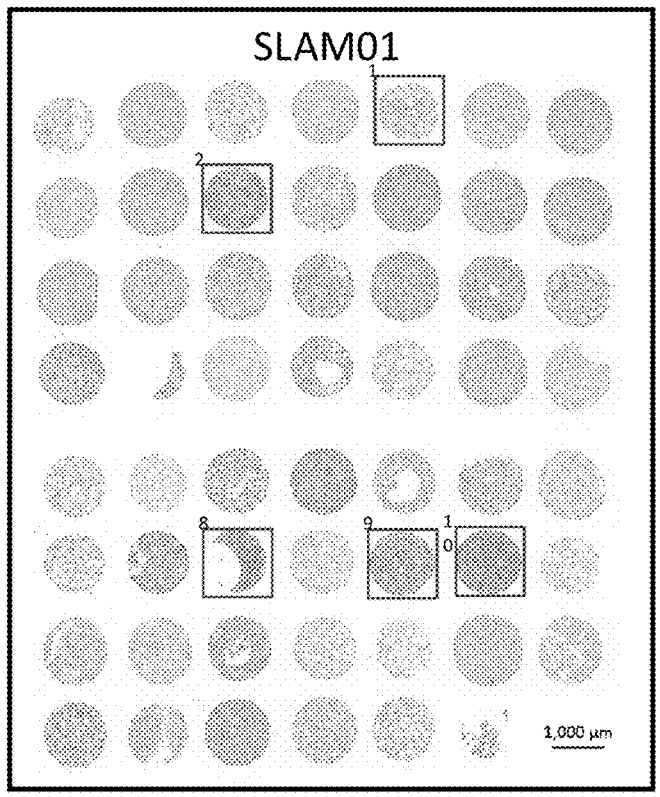

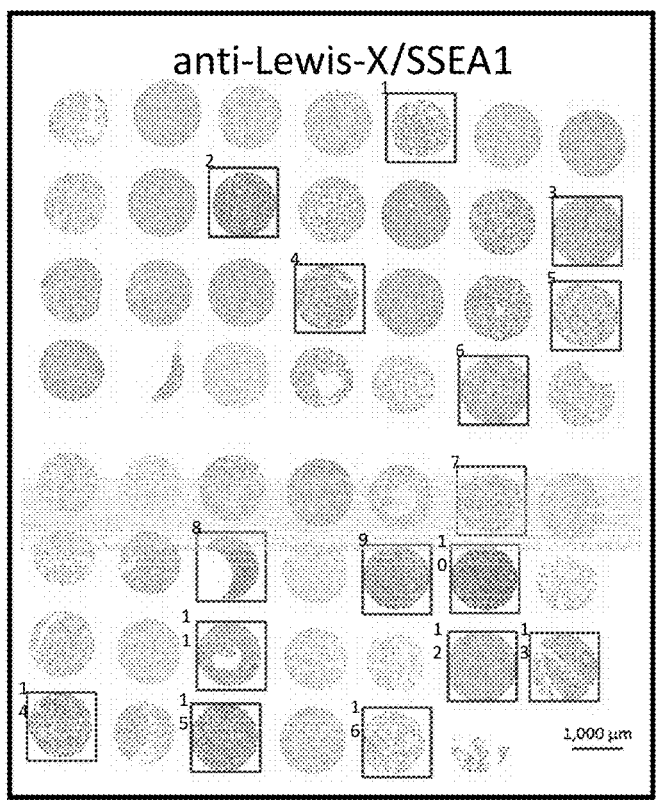

1. AGS (gastric adenocarcinoma)
2. CL-75 (non-small cell lung cancer)
3. H1299 (non-small cell lung cancer)
4. HCT15 (colorectal primary tumor)
5. Hep G2 (liver)
6. HT-29 (colorectal primary tumor)
7. MCF-7 (breast cancer, luminal A)
8. MONO-MAC-1 (acute myeloid leukemia)
9. OVCAR-3 (ovarian cancer)
10. PC-9 (non-small cell lung cancer)
11. SK-BR3 (breast cancer, HER2$^+$)
12. SKOV-3 (ovarian cancer)
13. SKOV-3-BIBF (BIBF treated ovarian cancer)
14. SW620 (colorectal metastatic lymph node)
15. THP-1 (acute myeloid leukemia)
16. TM-17 (head and neck cancer)

SEQUENCE LISTING

<160> NUMBER OF SEQ ID NOS: 8

<210> SEQ ID NO 1
<211> LENGTH: 10
<212> TYPE: PRT
<213> ORGANISM: Mus musculus

<400> SEQUENCE: 1

Gly Tyr Thr Phe Thr Ser Tyr Trp Ile His
1               5                   10

<210> SEQ ID NO 2
<211> LENGTH: 17
<212> TYPE: PRT
<213> ORGANISM: Mus musculus

<400> SEQUENCE: 2

Glu Ile Asn Pro Ser Asn Gly Arg Thr Asn Phe Asn Glu Lys Phe Lys
1               5                   10                  15

Asn

<210> SEQ ID NO 3
<211> LENGTH: 7
<212> TYPE: PRT
<213> ORGANISM: Mus musculus

<400> SEQUENCE: 3

Val Asp Tyr Asp Glu Ala Tyr
1               5

<210> SEQ ID NO 4
<211> LENGTH: 16
<212> TYPE: PRT
<213> ORGANISM: Mus musculus

<400> SEQUENCE: 4

Arg Ser Ser Lys Ser Leu Leu His Ser Asn Gly Ile Thr Tyr Leu Tyr
1               5                   10                  15

<210> SEQ ID NO 5
<211> LENGTH: 7
<212> TYPE: PRT
<213> ORGANISM: Mus musculus

<400> SEQUENCE: 5

Gln Met Ser Asn Leu Ala Ser
1               5

<210> SEQ ID NO 6
<211> LENGTH: 8
<212> TYPE: PRT
<213> ORGANISM: Mus musculus

<400> SEQUENCE: 6

Ala Gln Asn Leu Glu Leu Trp Thr
1               5

```
<210> SEQ ID NO 7
<211> LENGTH: 116
<212> TYPE: PRT
<213> ORGANISM: Mus musculus

<400> SEQUENCE: 7

Gln Val Lys Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asn Pro Ser Asn Gly Arg Thr Asn Phe Asn Glu Lys Phe
    50                  55                  60

Lys Asn Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Val Asp Tyr Asp Glu Ala Tyr Trp Gly Gln Gly Thr Thr Val
            100                 105                 110

Thr Val Ser Ser
        115

<210> SEQ ID NO 8
<211> LENGTH: 111
<212> TYPE: PRT
<213> ORGANISM: Mus musculus

<400> SEQUENCE: 8

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110
```

ANTI OLIGOSACCHARIDE ANTIBODY

CROSS-REFERENCE TO RELATED APPLICATIONS

A Sequence Listing, which is a part of the present disclosure, is submitted concurrently with the specification as a text file. The name of the text file containing the Sequence Listing is "52496_Seqlisting.txt." The Sequence Listing was created on Sep. 26, 2019, and is 3,443 bytes in size. The subject matter of the Sequence Listing is incorporated herein in its entirety by reference.

This application claims the benefit of priority of Singapore application No. 10201702572P, filed 29 Mar. 2017, the contents of it being hereby incorporated by reference in its entirety for all purposes.

FIELD OF THE INVENTION

The invention is in the field of antibodies, in particular antibodies specific for oligosaccharides of the Lewis X type.

BACKGROUND OF THE INVENTION

Hematological malignancies encompass a wide spectrum of cancers from hematopoietic and lymphoid tissues. Under this grouping, the various forms of leukemia, lymphoma and myeloma have been classified into more than 60 distinct disease types, each having particular clinical features and disease outcomes. Among these diseases, curative treatments with high long-term survival rate have been developed for some, e.g. Chronic Myeloid Leukemia, while such effective regimens are still unavailable for many others, e.g. Multiple Myeloma (MM) and Acute Myeloid Leukemia (AML).

Accordingly, there is a need for more effective treatment regimens for leukemia, lymphoma and myeloma.

SUMMARY

According to one aspect, there is provided an antigen-binding protein, or an antigen-binding fragment thereof, comprising (i) a heavy chain variable domain comprising a VHCDR1 having the amino acid sequence GYTFTSYWIH (SEQ ID NO:1); a VHCDR2 having the amino acid sequence EINPSNGRTNFNEKFKN (SEQ ID NO:2) and a VHCDR3 having the amino acid sequence VDYDEAY (SEQ ID NO:3); and (ii) a light chain variable domain comprising a VLCDR1 having the amino acid sequence RSSKSLLHSNGITYLY (SEQ ID NO:4), a VLCDR2 having the amino acid sequence QMSNLAS (SEQ ID NO:5), and a VLCDR3 having the amino acid sequence AQNLELWT (SEQ ID NO:6).

According to another aspect, there is provided a composition comprising a physiologically acceptable carrier and a therapeutically effective amount of the antigen-binding protein, or an antigen-binding fragment thereof, as described herein.

According to another aspect, there is provided a use of an antigen-binding protein, or an antigen-binding fragment thereof, as described herein or composition as described herein, in the manufacture of a medicament for treating or preventing cancer.

According to another aspect, there is provided a method for detecting cancer in a subject, the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample is indicative of cancer.

According to another aspect, there is provided a method for identifying a subject susceptible to cancer the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample indicates that the subject is susceptible to cancer.

According to another aspect, there is provided a kit when used in the method as described herein, comprising an antigen-binding protein, or antigen-binding fragment thereof as described herein, together with instructions for use.

Definitions

The term "antigen binding protein" as used herein refers to antibodies, antibody fragments and other protein constructs, such as domains, which are capable of binding to SLAMF7.

The term "antibody" is used herein in the broadest sense to refer to molecules with an immunoglobulin-like domain and includes monoclonal, recombinant, polyclonal, chimeric, humanised, bispecific and heteroconjugate antibodies; a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

The phrase "single variable domain" refers to an antigen binding protein variable domain (for example, $V_H$, $V_{HH}$, $V_L$) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

An antigen binding fragment may be provided by means of arrangement of one or more CDRs on non-antibody protein scaffolds such as a domain. The domain may be a domain antibody or may be a domain which is a derivative of a scaffold selected from the group consisting of CTLA-4, lipocalin, SpA, an Affibody, an avimer, GroEI, transferrin, GroES and fibronectin/adnectin, which has been subjected to protein engineering in order to obtain binding to an antigen other than the natural ligand.

Neutralisation may be determined or measured using one or more assays known to the skilled person or as described herein. For example, antigen binding protein binding to SLAMF7 can be assessed in a sandwich ELISA, by BIAcore™, FMAT, FORTEbio, or similar in vitro assays.

An antigen binding fragment or an immunologically effective fragment may comprise partial heavy or light chain variable sequences. Fragments are at least 5, 6, 8 or 10 amino acids in length. Alternatively the fragments are at least 15, at least 20, at least 50, at least 75, or at least 100 amino acids in length.

The term "specifically binds" as used throughout the present specification in relation to antigen binding proteins means that the antigen binding protein binds to an oligosaccharide of the Lewis X type, with no or insignificant binding to other (for example, unrelated) oligosaccharides. The antibody described herein does not bind to sialylated Lewis X.

The term "an oligosaccharide of the Lewis X type" is intended to encompass subsets of the Lewis X oligosaccharide including bioactive conformations of different forms of the Lewis X oligosaccharide epitope. The term "bioactive conformation" is intended to encompass the relative orientation of the sugar rings and their side chain orientations with respect to the dihedral angles $\phi$ and $\psi$ around the glycosidic linkages in order to define a particular conformation of an oligosaccharide. It is an advantage of the antigen binding protein as described herein that it can bind to a bioactive conformation of the Lewis X oligosaccharide epitope different to that of commercially available (for example, anti-SSEA1 antibody) anti-Lewis X antibodies.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will be better understood with reference to the detailed description when considered in conjunction with the non-limiting examples and the accompanying drawings, in which:

FIG. 6 summarizes the binding profile of SLAM01 and anti-CD319 on various hematological cell lines. SLAM01 and Anti-CD319 was screened against 7 MM lines, 1 Burkitt's Lymphoma line and 14 AML lines. SLAM01 preferentially binds to AML lines but not MM or B cell lines.

FIG. 7 summarizes the binding profile of SLAM01 on solid tumour cell lines. SLAM01 is positive for non-small cell lung cancer cell line PC9; ovarian cancer cell lines OVCAR3 and SKOV3.

FIG. 8 summarizes the binding profile of SLAM01 on normal cell lines. SLAM01 does not bind to various normal cell lines tested.

FIG. 9 summarizes the immunohistochemistry binding profile of SLAM01 on in-house formalin-fixed paraffin-embedded (FFPE) cell line array. SLAM01 was negative for the normal cell lines. Besides being positive (2+ and 3+) for the AML line (F3), SLAM01 is also positive for some non-small cell lung cancer (NSCLC), ovarian, breast, gastric and colorectal cancer lines.

FIG. 10 shows the immunohistochemistry staining of SLAM01 on Mono-Mac-1 (AML) and PC9 (NSCLC), both cores from in house FFPE cell line array. SLAM01 binds strongly to Mono-Mac-1 (3+) and PC9 (3+).

FIG. 17 highlights the positive correlation of SLAM01 binding percentage and relative cytotoxicity on AML cell lines. SLAM01 was screened against these AML cell lines. Data on average binding percentage were collected via flow cytometry, while data on relative cytotoxicity were determined via Mab-Zap assay. The cell lines that were positive for SLAM01 binding (average binding percentage >20%) exhibit high cytotoxicity percentage when treated with SLAM01-Mab-Zap complex.

FIG. 21 shows the relative viability of AML-3 and Mono-Mac-1 after treating with various cSLAM01/Ig-toxin complex for 3 days. cSLAM01 was complexed with either Mab-ZAP, g-Monomethyl auristatin E (MMAE) or Ig-DM1 before treating AML3 and Mono-Mac-1. Controls were set up without cSLAM01. The reduced cell viability observed on cells treated with cSLAM01/Ig-toxin as compared to control, demonstrated that cSLAM01 retained the ADC potential.

FIG. 28 shows an immunohistochemical staining of SLAM01 and anti-Lewis-X/SSEA1 on FFPE cell line array.

DETAILED DESCRIPTION OF THE PRESENT INVENTION

Figure 1:
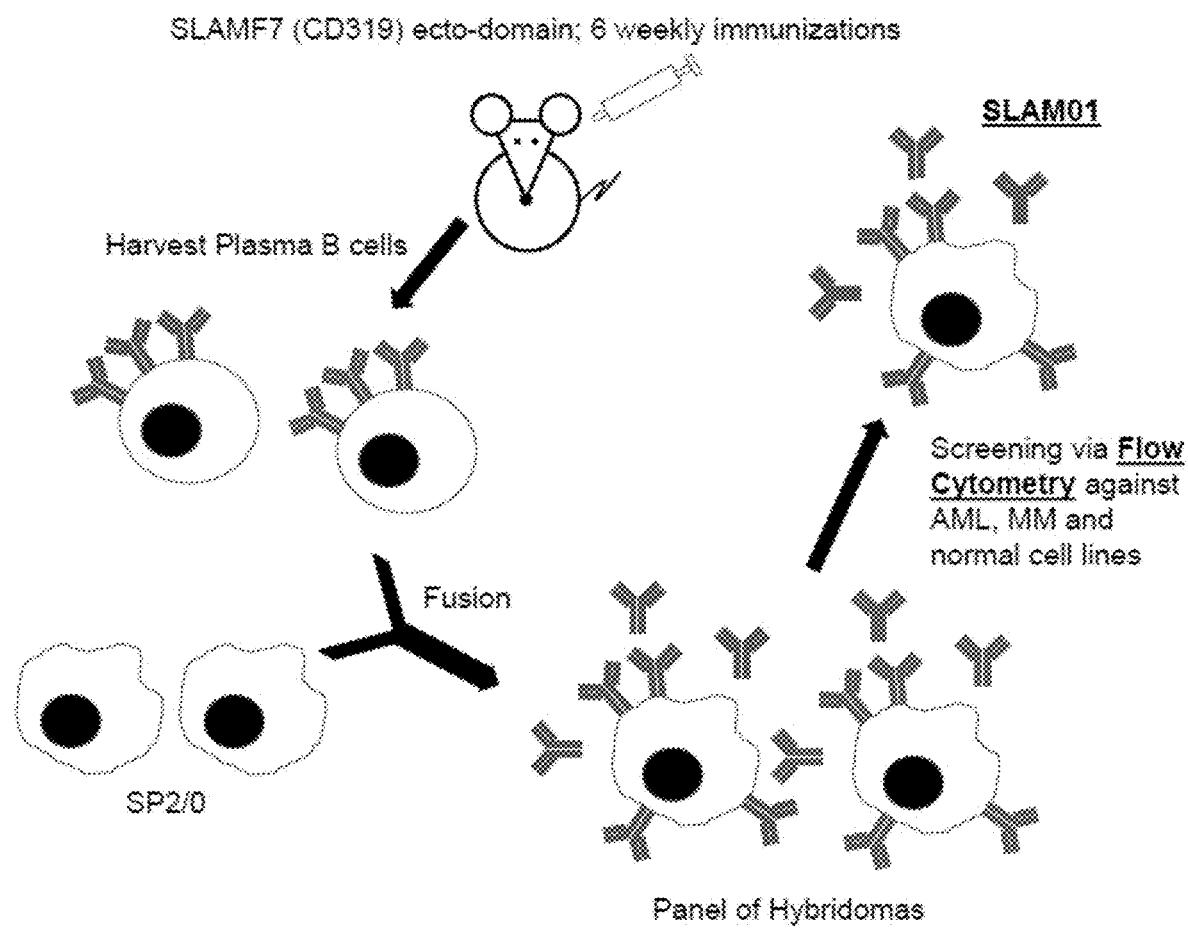
FIG. 1 shows the schematic workflow of mouse immunization, hybridoma fusion and screening.

In a first aspect the present invention refers to an antigen-binding protein, or an antigen-binding fragment thereof, comprising (i) a heavy chain variable domain comprising a VHCDR1 having the amino acid sequence GYTFTSYWIH (SEQ ID NO:1); a VHCDR2 having the amino acid sequence EINPSNGRTNFNEKFKN (SEQ ID NO:2) and a VHCDR3 having the amino acid sequence VDYDEAY (SEQ ID NO:3); and (ii) a light chain variable domain comprising a VLCDR1 having the amino acid sequence RSSKSLLHSNGITYLY (SEQ ID NO:4), a VLCDR2 having the amino acid sequence QMSNLAS (SEQ ID NO:5), and a VLCDR3 having the amino acid sequence AQNLELWT (SEQ ID NO:6).

The antigen-binding protein, or antigen-binding fragment thereof, may comprise heavy and light chain CDR regions that are about 80%, about 85%, about 90%, about 95%, about 96%, about 97%, about 98% or about 99% identical to the heavy and light chain CDR regions of (i) and (ii).

The heavy chain variable region may comprise the amino acid sequence

QVKLQQSGAELAKPGASVKLSCKASGYTFTSYWIHWVKQRPGQGLEWIGE
INPSNGRTNFNEKFKNKATLTVDKSSSTAYMQLNSLTSEDSAVYYCARVD
YDEAYWGQGTTVTVSS as set forth in SEQ ID NO: 7.

In some embodiments, the heavy chain variable region comprises an amino acid sequence having about 80%, about 85%, about 90%, about 95%, about 96%, about 97%, about 98% or about 99% identity to the amino acid sequence set forth in SEQ ID NO:7.

In some embodiments, the light chain variable region may comprise the amino acid sequence DIVMTQAAFSNPVTLGTSASISCRSSKSLLHSNGITYLYWYLQKPGQSPQ
LLIYQMSNLASGVPDRFSSSGSGTDFTLRISRVEAEDVGVYYCAQNLELW
TFGGGTKLEIK as set forth in SEQ ID NO: 8.

The light chain variable region may comprise an amino acid sequence having about 80%, about 85%, about 90%, about 95%, about 96%, about 97%, about 98% or about 99% identity to the amino acid sequence set forth in SEQ ID NO:8.

In one embodiment, the antigen binding protein is selected from the group consisting of monoclonal, recombinant, polyclonal, chimeric, humanised, bispecific and heteroconjugate antibodies; a single variable domain, a domain antibody, antigen binding fragments, immunologically effective fragments, single chain Fv, a single chain antibody, a univalent antibody lacking a hinge region, a minibody, diabodies, and Tandabs™.

In some embodiments, the binding protein is a monoclonal antibody. In one embodiment the monoclonal antibody is SLAM01.

The monoclonal antibody described herein may be humanised. Alternatively, the monoclonal antibody is chimeric.

In one embodiment, the antigen-binding protein, or antigen-binding fragment thereof, as described herein, binds to an N-linked glycan. The N-linked glycan maybe located on an extracellular portion of SLAMF7. The N-linked glycan may be an oligosaccharide of the Lewis X type. In some embodiments, the antigen-binding protein, or antigen-binding fragment thereof, as described herein, does not bind to an oligosaccharide of the sialylated Lewis X type.

In one embodiment, the antigen-binding protein, or antigen-binding fragment thereof, as described herein may comprise a radioisotope or a cytotoxin conjugated thereto.

The antigen-binding protein, or antigen-binding fragment thereof, as described herein may be conjugated with a cytotoxin selected from the group consisting of monomethyl auristatin E (MMAE-1), mertansine (DM-1), saporin, gemcitabine, irinotecan, etoposide, vinblastine, pemetrexed, docetaxel, paclitaxel, platinum agents (for example, cisplatin, oxaliplatin and carboplatin), vinorelbine, capecitabine, mitoxantrone, ixabepilone, eribulin, 5-fluorouracil, trifluridine and tipiracil.

In some embodiments, the antigen-binding protein, or an antigen-binding fragment thereof, may be internalized into a cell upon binding to said N-linked glycan on SLAMF7.

In some embodiments, the antigen-binding protein, or an antigen-binding fragment may selectively binds to a non-small cell lung cancer cell, an ovarian cancer cell, a breast cancer cell, an acute myeloid leukemia cell and a colorectal cancer cell.

In another aspect the present disclosure provides a composition comprising a physiologically acceptable carrier and a therapeutically effective amount of the antigen-binding protein, or an antigen-binding fragment thereof, as described herein.

In some embodiments, the composition as described herein may comprise one or more further therapeutic compounds.

In another aspect, the present disclosure provides the use of an antigen-binding protein, or an antigen-binding fragment thereof, as described herein or composition as described herein, in the manufacture of a medicament for treating or preventing cancer.

The cancer may be selected from the group consisting of non-small cell lung cancer, ovarian cancer, breast cancer, acute myeloid leukemia and colorectal cancer.

In one embodiment, the medicament may be administered with one or more further active pharmaceutical ingredients.

In another embodiment, the medicament may be administered with chemotherapy.

The one or more further pharmaceutical agents or chemotherapy may be administered separately, simultaneously or sequentially with said medicament.

In another aspect, the present disclosure provides a method for detecting cancer in a subject, the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample is indicative of cancer.

In another aspect, the present disclosure provides a method for identifying a subject susceptible to cancer the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample indicates that the subject is susceptible to cancer.

In some embodiments, the control sample may be from the same subject. Alternatively, the control sample may be from a different subject.

The antigen-binding protein, or antigen-binding fragment thereof, may comprise a detectable label. In some embodiments, the detectable label may be selected from the group consisting of a fluorescent label, a chemiluminescent label, an enzymatic label and a radionuclide label. The detectable label may be selected from the group consisting of biotin, alkaline phosphatase, horseradish peroxidase, FITC, PE and Cy Dyes.

In some embodiments, the detectable label may be detected in an assay selected from flow cytometry, tissue section, immunofluorescence, immunocytochemistry or immunohistochemistry.

In one embodiment, the cancer may be selected from the group consisting of non-small cell lung cancer, ovarian cancer, breast cancer, acute myeloid leukemia and colorectal cancer.

In another aspect, the present disclosure provides a kit when used in the method as described herein, comprising an antigen-binding protein, or antigen-binding fragment thereof as described herein, together with instructions for use.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Example 1. Immunization and Generation of mAbs

In this study, a panel of monoclonal antibodies (mAbs) was raised against SLAMF7 (CD319), a cell surface marker that is associated to MM. To generate these mAbs, 4 female BALB/c mice were immunized with recombinant human SLAMF7 (CD319) purchased from Sino Biological Inc. (Catalogue No. 11691-H08H) (FIG. 1). The DNA sequence that encodes the recombinant human SLAM7 (CD319), consists of an extracellular domain (Met1 to Met226) fused with a polyhistidine tag at the C-terminus, that was expressed via human host cells.

Mice immunization started on 6 Feb. 2014, and this was followed by an immunisation regime consisting of 5 weekly immunisations and 1 booster immunisation. Upon completion of the immunisation regime, plasma B cells were harvested and fused with SP2/0 mouse myeloma lines on 13 Mar. 2014 (FIG. 1). Hybridoma fusion was performed using STEMCELL Technologies ClonaCell™-HY kit and generated a panel of hybridomas that produces mAbs present in the culture supernatant. The mAbs were screened by flow cytometry for binding with AML, MM, other cancer and normal cell lines, that subsequently identified a novel anti-SLAMF7 antibody, SLAM01.

Example 2. Binding Profile of SLAM01 mAb

Figure 2:
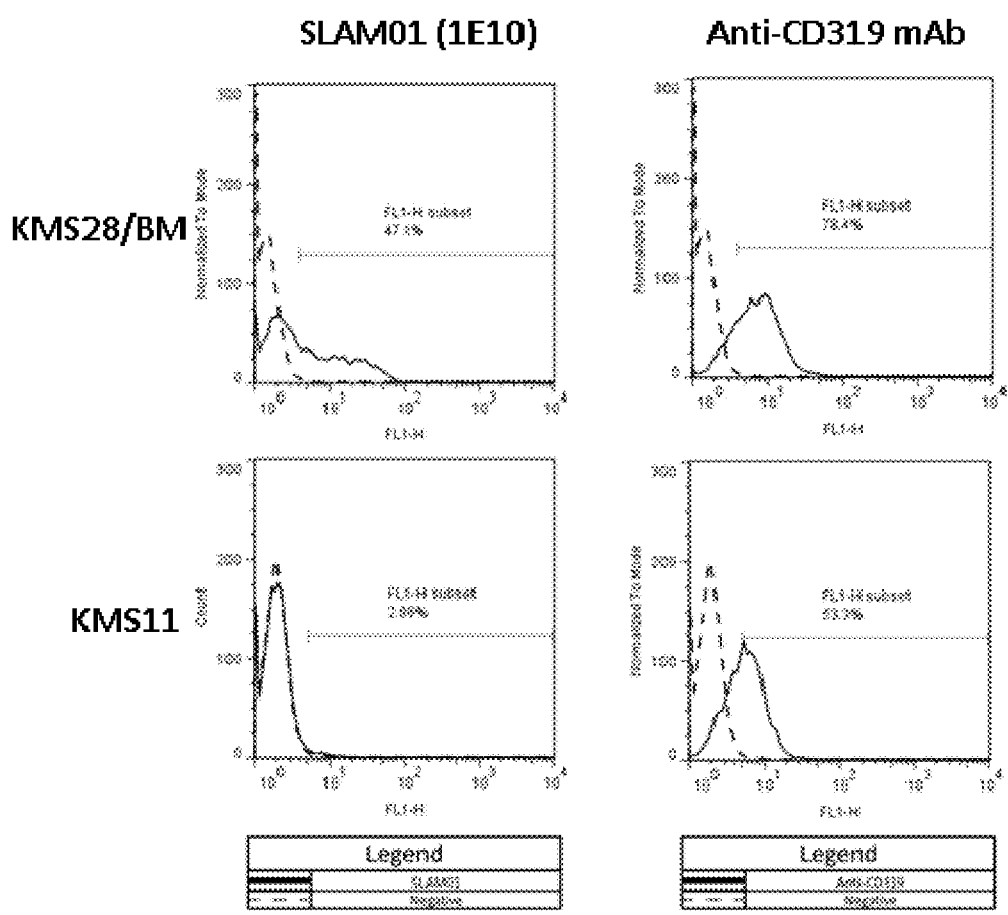
FIG. 2 shows the binding of SLAM01 (1E10) and commercial anti-CD319 on MM cell lines: KMS28/BM and KMS11. SLAM01 binds only to KMS28/BM but not KMS11, despite the expression of CD319 (SLAMF7) on both cell lines.
Figure 3:
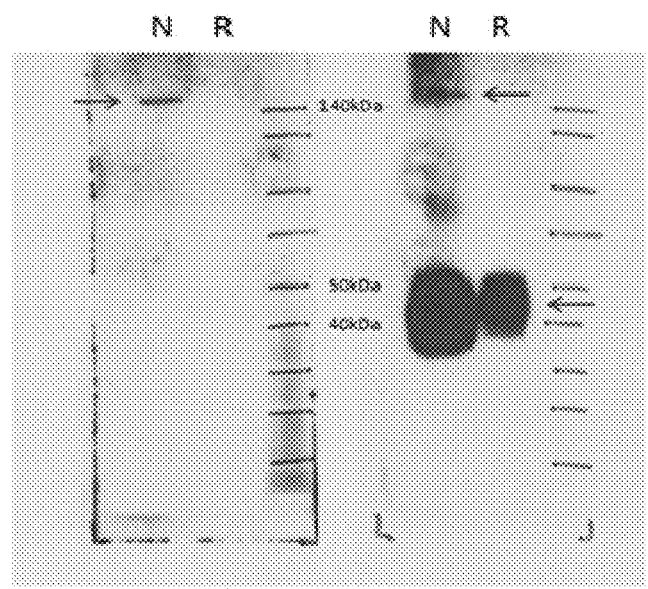
FIG. 3 shows an immunoblot of SLAM01 and anti-CD319 on ectodomain of CD319. SLAM01 only recognized a high molecular weight form (>140 kDa) of CD319 ectodomain under non-reducing condition (N), but not in reducing (R) condition. SLAM01 does not recognise the predicted size of SLAMF7 between 40 to 50 kDa (as probed by anti-CD319).
Figure 4:
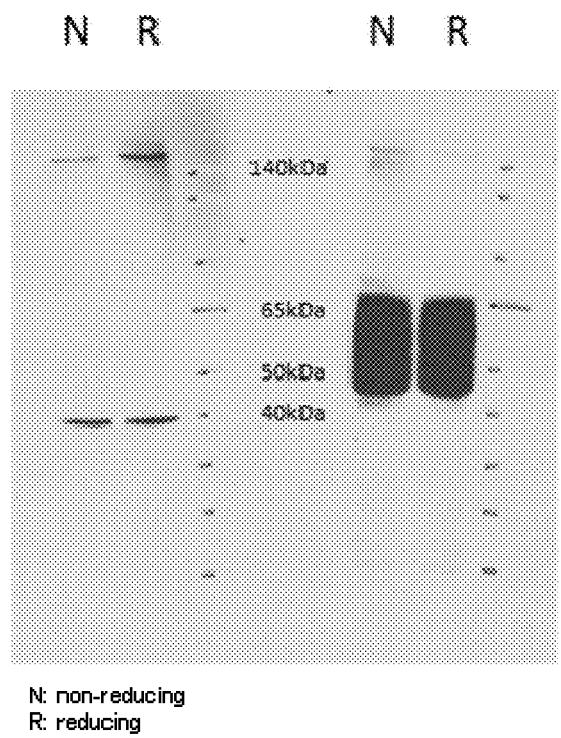
FIG. 4 shows an immunoblot of SLAM01 and anti-CD319 on KMS28/BM lysate. SLAM01 recognized the high molecular weight form and a 40 kDa form of CD319 on KMS28/BM lysate and not the expected size of the smear of full length CD319, which is between 40 to 65 kDa.
Figure 5:
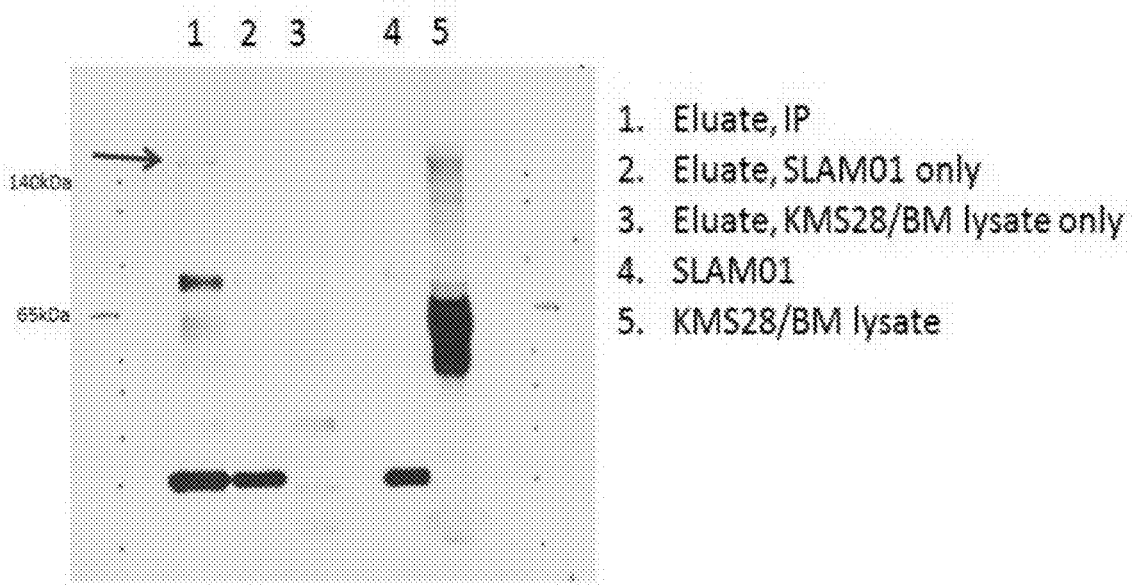
FIG. 5 shows an immunoblot of SLAM01-immunoprecipitated (IP) product by anti-CD319. KMS28/BM lysate was immunoprecipitated with SLAM01 and the eluate was immunoblotted with anti-CD319. The high molecular weight band was observed on lane 1 (IP eluate) and lane 5 (KMS28/BM lysate).

Flow cytometry analysis of 1E10 mAb (SLAM01) on MM cell lines expressing CD319 (SLAMF7) indicates binding of SLAM01 to KMS28/BM but not KMS11 (FIG. 2). The binding between SLAM01 and high molecular weight form (>140 kDa) of CD319 ectodomain was observed by immunoblotting under non-reducing condition only (FIG. 3). Based on the immunoblot probed by anti-CD319 Ab, SLAM01 also does not recognize the predicted size of SLAMF7 between 40 to 50 kDa. The recognition of SLAM01 to the full length form of CD319 was assessed by immunoblotting SLAM01 with KMS28/BM lysate under both non-reducing and reducing conditions (FIG. 4). The immunoblot shows that SLAM01 recognized both the high molecular weight and 40 kDa forms of CD319. However, SLAM01 does not recognize the entirety of the full length form of CD319 that appears as a smear (40 to 65 kDa) on the immunoblot with anti-CD319. To further confirm the recognition of SLAM01 to CD319, KMS28/BM lysate was immunoprecipitated (IP) with SLAM01 and the eluate was immunoblotted with anti-CD319 Ab (FIG. 5). The immunoblot indicated binding of anti-CD319 Ab to the high molecular weight form of CD319 in both IP eluate (lane 1) and KMS28/BM lysate (lane 5). Thus, SLAM01 recognized the high molecular weight form of CD319.

Among the mAbs, SLAM01 was surprisingly found to preferentially bind to SLAMF7 expressed on AML cell lines rather than MM (FIG. 6). In addition, SLAM01 demonstrates reactivity to several ovarian and NSCLC cell lines by flow cytometry (FIG. 7). SLAM01 does not have non-specific binding to fibroblast, epithelial cell lines, adult MSC and PBMC when tested via flow cytometry (FIG. 8). To further confirm the reactivity of SLAM01 on the cell lines, immunohistochemistry was performed on in-house FFPE cell line array, and results were scored by ImmunoMembrane. The human cell line array showed that SLAM01 had high selectivity to the tumor antigen target on many AML cell lines and other cancer cell lines, such as breast, ovarian, gastric, colorectal and NSCLC, while no staining was observed on normal cell lines (FIGS. 9 and 10). Thus, both flow cytometry and immunohistochemistry revealed the preferential binding of SLAM01 to AML and other cancer cell lines, and not to MM, B cell lines or normal cells.

Example 3. Determination of SLAM01 Isotype and Epitope Nature

Figure 11:
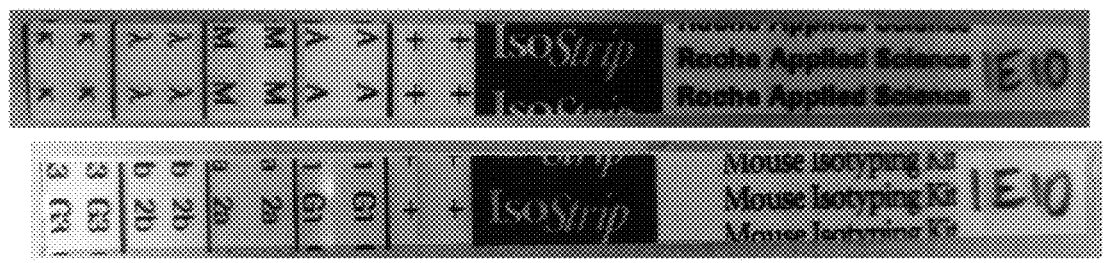
FIG. 11 shows the isotype of SLAM01. SLAM01 was determined to be an IgM with κ light chain.

SLAM01 was isotyped and determined to be a mouse IgM monoclonal antibody of κ isotype (FIG. 11). The translated sequence of the variable heavy and light chains, with the complementarity-determining regions (CDRs) underlined, are as follows:

```
Variable heavy chain
                                           (SEQ ID NO: 7)
QVKLQQSGAE LAKPGASVKL SCKASGYTFT SYWIHWVKQR
PGQGLEWIGE INPSNGRTNF NEKFKNKATL TVDKSSSTAY
MQLNSLTSED SAVYYCARVD YDEAYWGQGT TVTVSS Variable light chain
                                           (SEQ ID NO: 8)
DIVMTQAAFS NPVTLGTSAS ISCRSSKSLL HSNGITYLYW
YLQKPGQSPQ LLIYQMSNLA SGVPDRFSSS GSGTDFTLRI
SRVEAEDVGV YYCAQNLELW TFGGGTKLEI K
```

Figure 12:
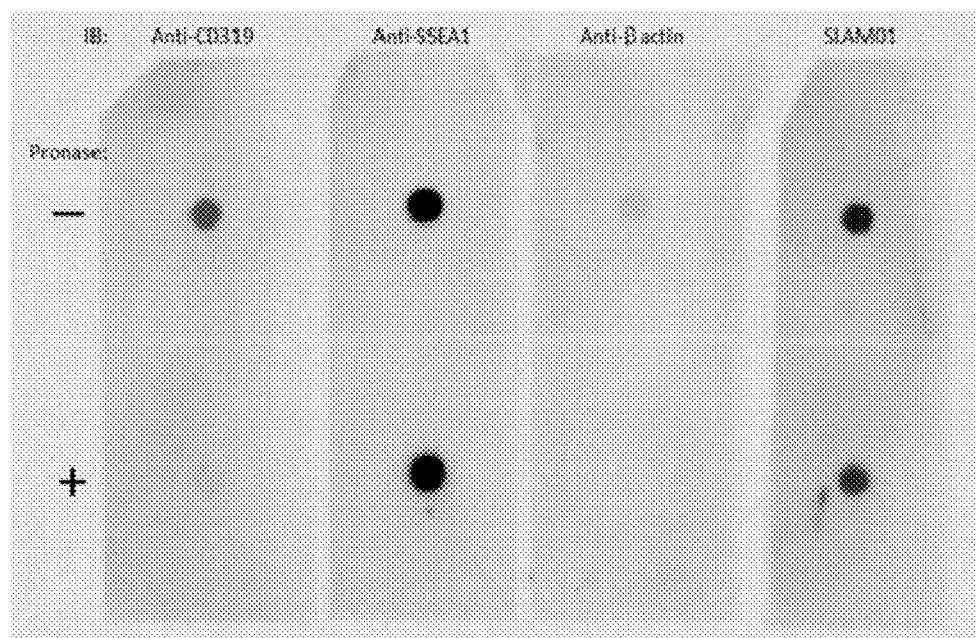
FIG. 12 shows an immunoblot of SLAM01 on pronase-treated AML3 lysate. AML3 lysate was treated with pronase to digest the proteins in it. Control lysate was set up without the pronase enzyme. After digestion, the lysates were dotted onto membrane and allowed to dry before immunoblot with either anti-CD319 mAb, anti-SSEA1 mAb, anti-β-actin mAb or SLAM01. Binding of SLAM01 on pronase-treated lysate was similar to that of control, indicating that the binding of SLAM01 was not affected with the loss of protein and structure. This demonstrated that SLAM01 is binding to a glycan epitope.
Figure 13:
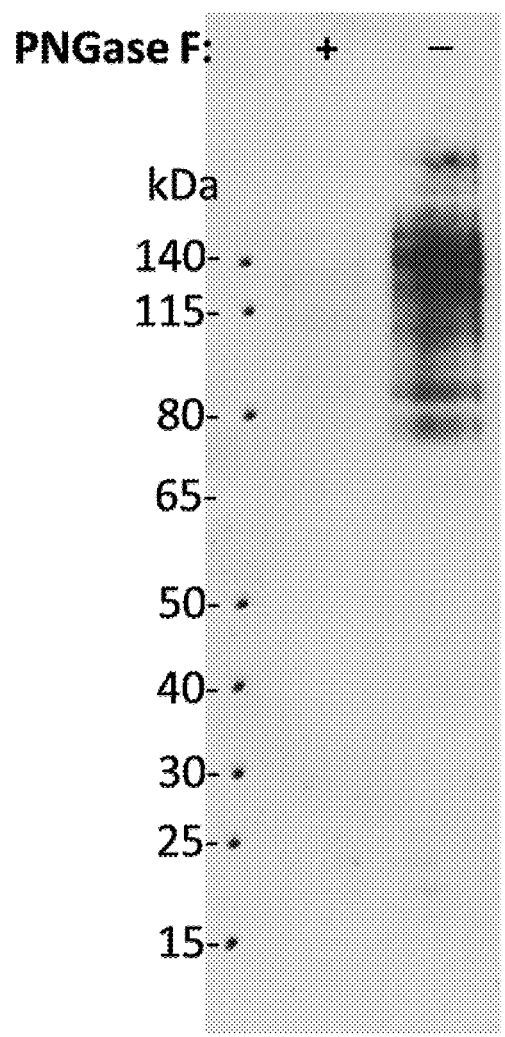
FIG. 13 shows an immunoblot of SLAM01 on OCI-AML3 lysate treated with PNGase. OCI-AML3 lysate was treated with PNGase F to remove N-linked glycan. Binding of SLAM01 to OCI-AML3 lysate was lost after PNGase F treatment; concluding that SLAM01 binding requires N-linked glycan on the antigen.
Figure 14:
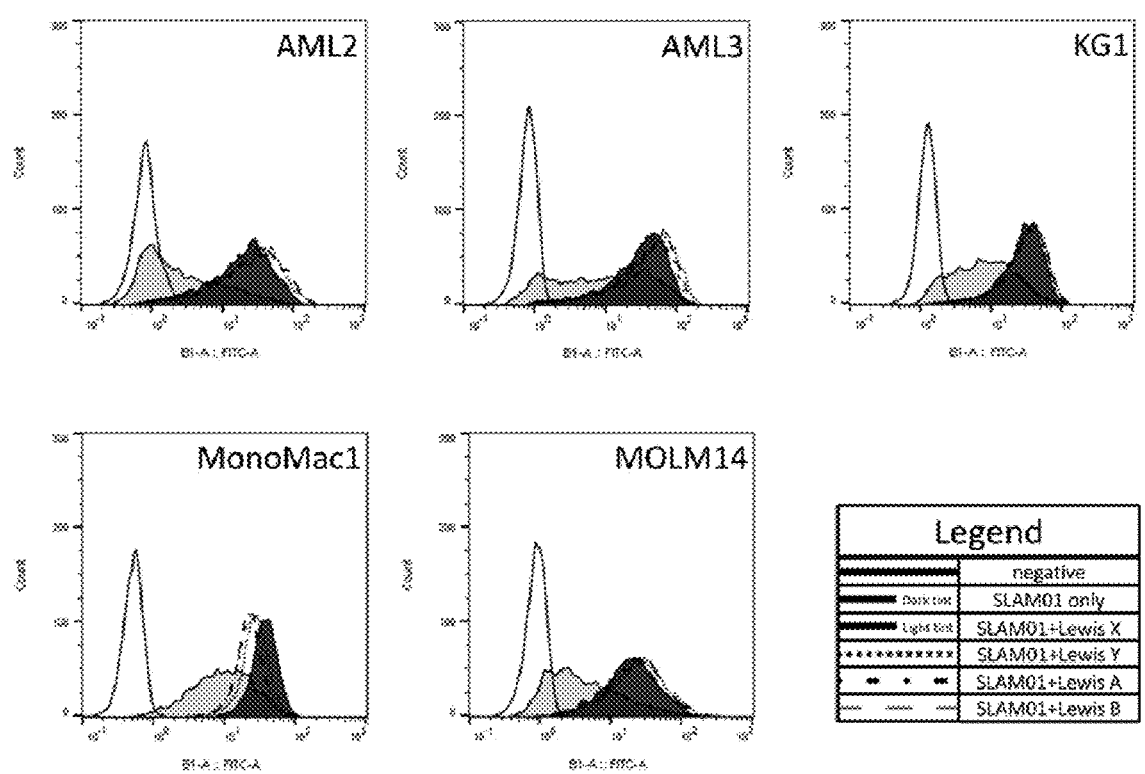
FIG. 14 shows the competitive binding of SLAM01 on various AML cell lines. SLAM01 was pre-incubated with free Lewis X ($Le^X$), Lewis Y ($Le^Y$), Lewis A ($Le^A$) and Lewis B ($Le^B$) separately for 30 min. Each SLAM01-glycan mix was then tested for binding against five AML cell lines (AML2, AML3, KG1, MOLM14 and Mono-Mac-1). Only SLAM01 pre-incubated with $Le^X$ displayed significantly reduced binding percentage as compared to positive control (SLAM01 without glycan) across all 5 lines. This concludes that SLAM01 recognizes glycan with terminal $Le^X$ structure.

Epitope characterization revealed that SLAM01 recognized a glycan epitope as binding was not affected after AML3 was treated with pronase, an enzyme that digests protein to amino acid (FIG. 12). In addition, SLAM01 required the presence of N-linked glycan for binding (FIG. 13). SLAM01 binding to the antigen was abolished with PNGase treatment (lane 1), indicating the requirement of N-glycan for binding. In addition, pre-incubation of SLAM01 with $Le^X$ resulted in reduced binding of SLAM01 to all AML cell lines. (FIG. 14). Thus, SLAM01 is a mouse IgM monoclonal antibody that recognizes terminal $Le^X$ structure on N-glycosylated SLAMF7 on human cancer cells, with a defined translated protein sequence encoding the variable heavy and light antibody chains.

Figure 24:
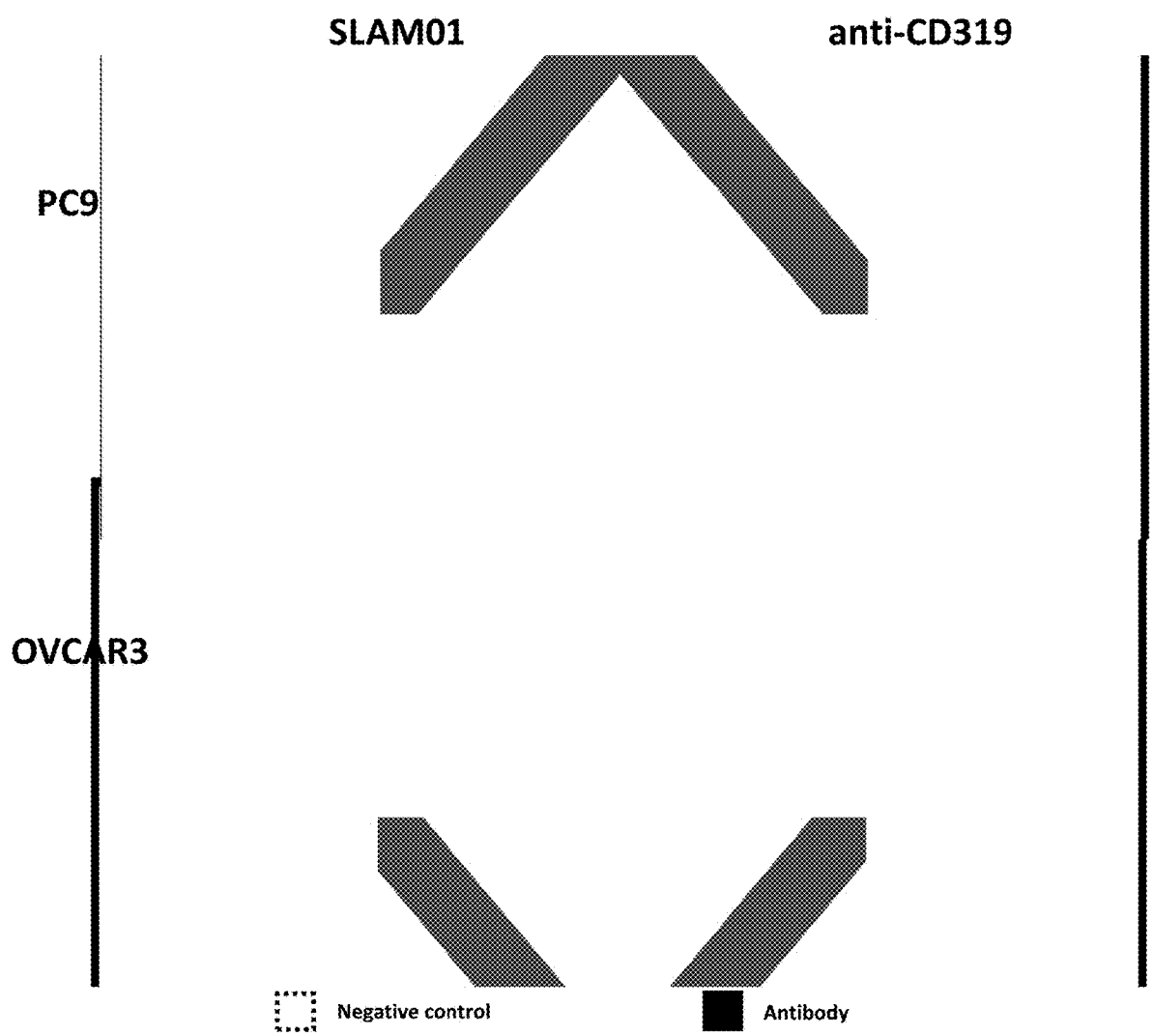
FIG. 24 shows a flow cytometry histogram of SLAM01 and anti-CD319 on PC9 and OVCAR3 cell lines. PC9 (non-small cell lung cancer cell line) and OVCAR3 (epithelial ovarian cancer cell line) were incubated with either SLAM01 or anti-CD319 to test for expression of the respective antigen on cell surface.

To further characterize the binding of SLAM01 to SLAMF7 PC9 (non-small cell lung cancer cell line) and OVCAR3 (epithelial ovarian cancer cell line) were incubated with either SLAM01 or anti-CD319 to test for expression of the respective antigen on cell surface. The histograms in FIG. 24 showed that the 2 cell lines are positive for SLAM01 but negative for CD319. This suggests that the epitope that SLAM01 is binding to on PC9 and OVCAR3, is not on CD319.

Figure 25:
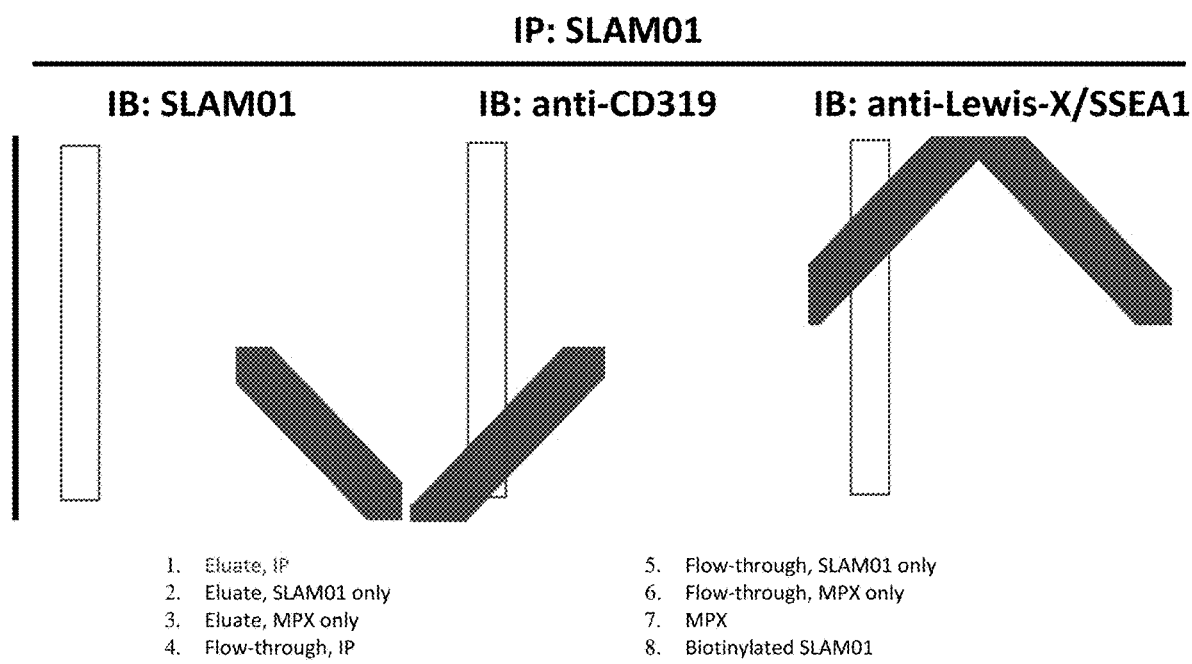
FIG. 25 shows western blots of SLAM01, anti-CD319 and anti-Lewis-X/SSEA1 on SLAM01-immunoprecipitated proteins. OCI-AML3 membrane protein extracts (MPXs) were immunoprecipitated with SLAM01. The immunoprecipitated proteins were resolved via SDS-PAGE and immunoblotted with SLAM01, anti-CD319 and anti-Lewis-X/SSEA1.

Western blots of SLAM01, anti-CD319 and anti-Lewis-X/SSEA1 on SLAM01-immunoprecipitated proteins we prepared (FIG. 25). OCI-AML3 membrane protein extracts (MPXs) were immunoprecipitated with SLAM01 and the immunoprecipitated proteins were resolved via SDS-PAGE and immunoblotted with SLAM01, anti-CD319 and anti-Lewis-X/SSEA1. The blots showed that SLAM01 has successfully immunoprecipitated the proteins from the MPX (left immunoblot, Lane 1). However, the immunoprecipitated proteins are not recognized by anti-CD319 (middle immunoblot, Lane 1) despite the expression of CD319 by OCI-AML3 (middle immunoblot, Lane 7). These SLAM01-immunoprecipitated proteins are modified with Lewis-X (right immunoblot, Lane 1). These data demonstrate that SLAM01 does not recognize CD319, but glycoproteins with Lewis-X.

Figure 26:
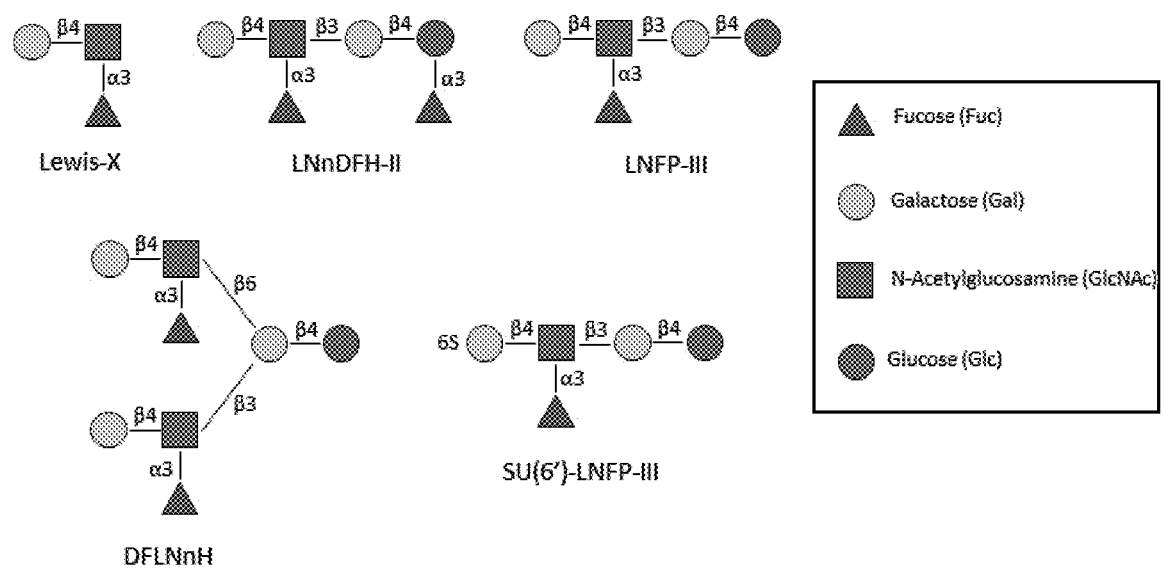
FIG. 26 shows a 2D representation of glycan structures that were positive for SLAM01.

2D representations of glycan structures that were positive for SLAM01 can be seen in FIG. 26. SLAM01 was found to be positive for Lewis-X and also 4 glycan structures that contain Lewis-X structure at the terminal, non-reducing end of glycan structure.

Figure 27:
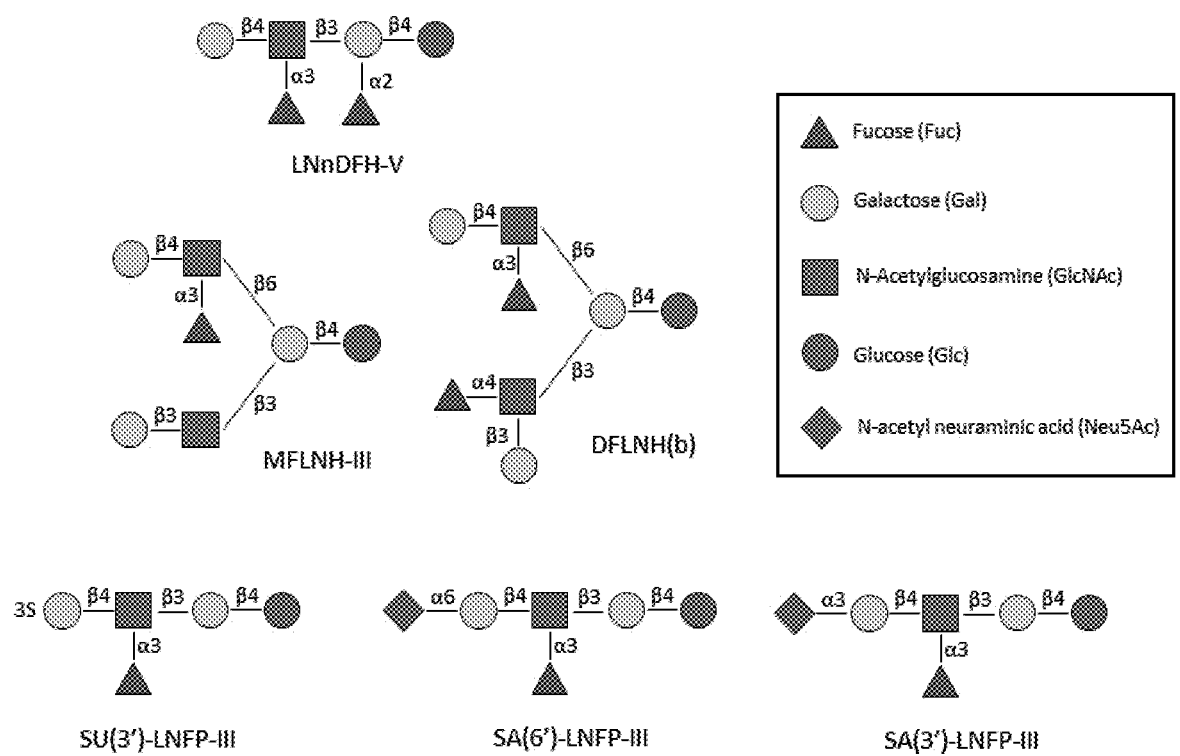
FIG. 27 shows a 2D representation of glycan structures that were negative for SLAM01.

2D representations of glycan structures that were negative for SLAM01 can be seen in FIG. 27. SLAM01 was negative for these glycan structures that contain Lewis-X structure at the terminal, non-reducing end of glycan structure. From this data, it is hypothesized, albeit in no way limiting, that binding of SLAM01 requires Lewis-X to be presented on a specific glycan backbone or SLAM01 recognizes an epitope that consist of terminal Lewis-X structure and other glycans.

SLAM01 and anti-Lewis-X/SSEA1 were stained on an in-house FFPE cell line array (FIG. 28). SLAM01 stained 5/48 of the cell line cores while anti-Lewis-X/SSEA1 stained 16/48 cores. All SLAM01-positive cores were positive for Lewis-X, supporting the hypothesis that SLAM01 is recognizing either Lewis-X on specific glycan backbone or SLAM01 epitope consist of terminal Lewis-X structure and other glycans.

Figure 29:
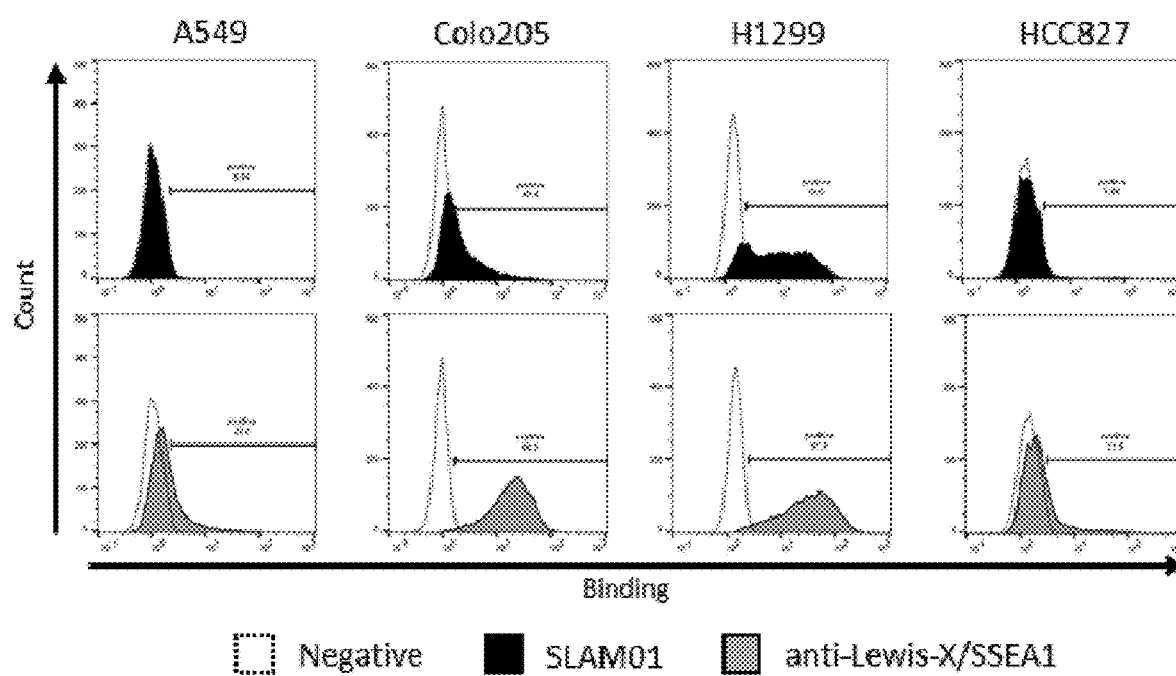
FIG. 29 shows binding histograms of SLAM01 and anti-Lewis-X/SSEA1 on A549, Colo205, H1299 and HCC827. SLAM01 and anti-Lewis-X/SSEA1 were incubated on A549 (lung cancer cell line), Colo205 (colorectal cancer cell line), H1299 (lung cancer cell lines) and HCC827 (lung cancer cell line) to determine their cell surface expression profiles.

SLAM01 and anti-Lewis-X/SSEA1 were incubated on A549 (lung cancer cell line), Colo205 (colorectal cancer cell line), H1299 (lung cancer cell lines) and HCC827 (lung cancer cell line) to determine their cell surface expression profiles (FIG. 29). SLAM01 had different expression profiles than that of anti-Lewis-X/SSEA1 across all 4 cell lines, suggesting that SLAM01 is recognizing either Lewis-X on a specific glycan backbone or SLAM01 epitope consists of a terminal Lewis-X structure and other glycans.

Example 4. ADC Potential of SLAM01

Figure 15:
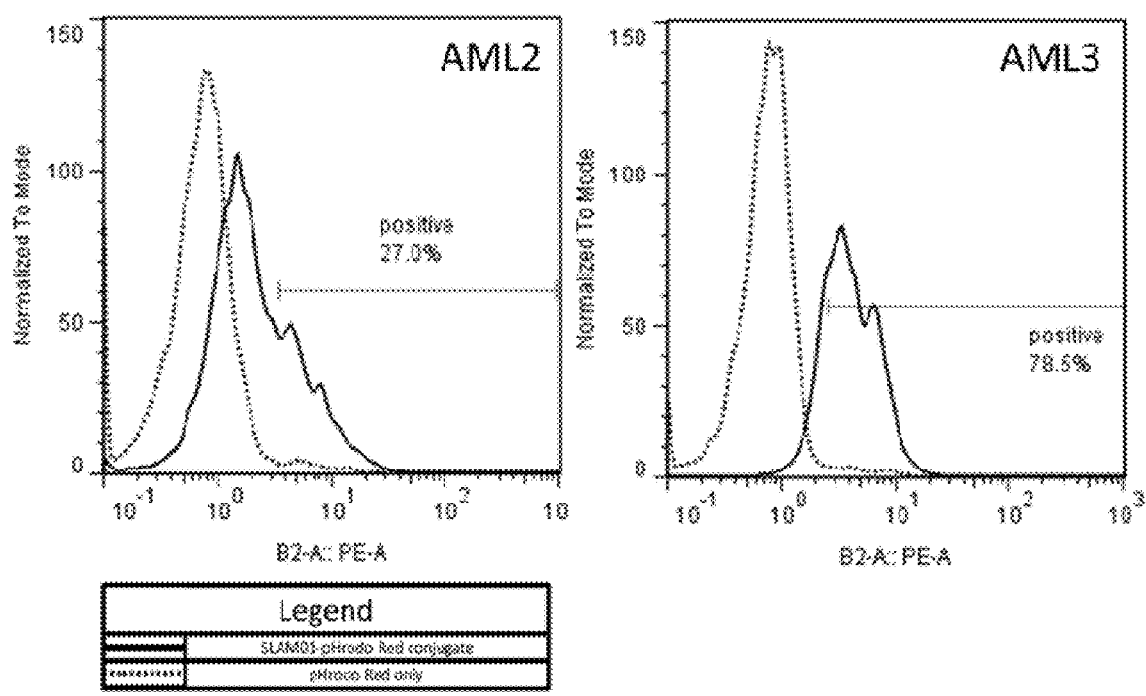
FIG. 15 shows the binding profile of SLAM01-pHrodo Red conjugate on AML2 and AML3. pHrodo Red dye fluoresces in acidic condition such as in endosome. AML2 and AML3 that were incubated with pHrodo Red conjugated SLAM01 for 60 min at room temperature displayed increased fluorescence as compared to control. This indicates that SLAM01-pHrodo Red dye was internalised into endosome.
Figure 16:
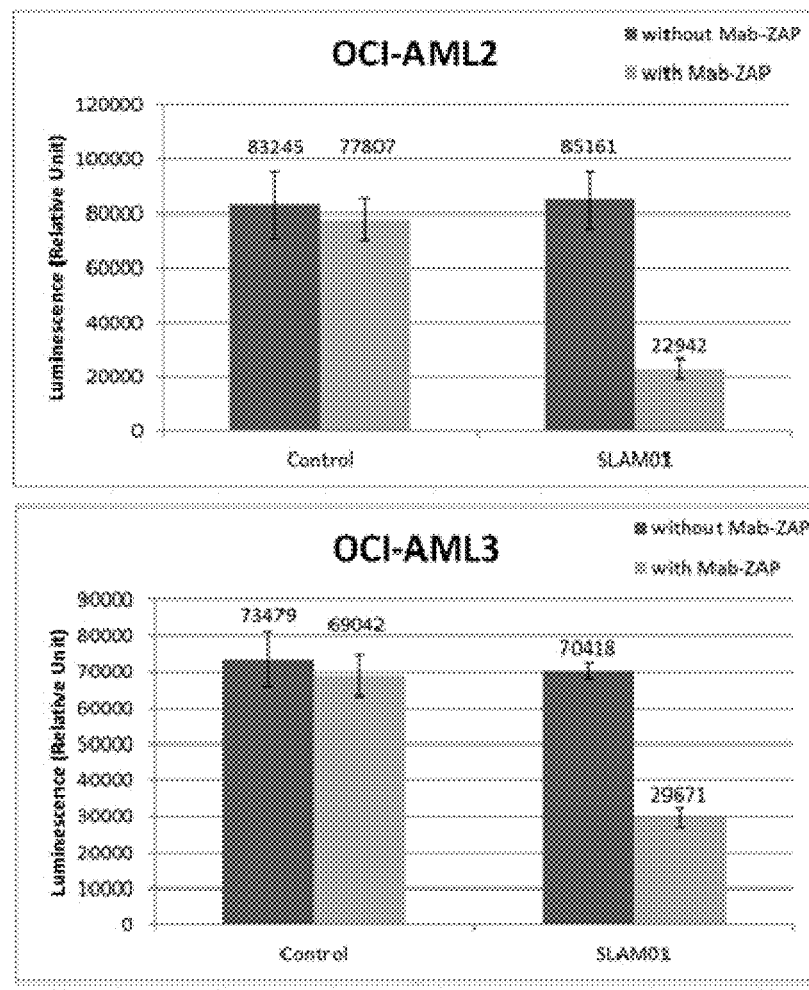
FIG. 16 shows the relative viability of AML-2 and -3 after treating with SLAM01-Mab-ZAP complex for 3 days. Mab-ZAP is a secondary anti-mouse antibody conjugated with saporin. Saporin when internalised into the cytoplasm affects protein translation and results in cell death. A reduced cell viability was observed only for cells treated with SLAM01-Mab-Zap complex ($1^{st}$ column from right). This concludes that SLAM01 can deliver a toxic payload into cells resulting in cell killing as an ADC.
Figure 18:
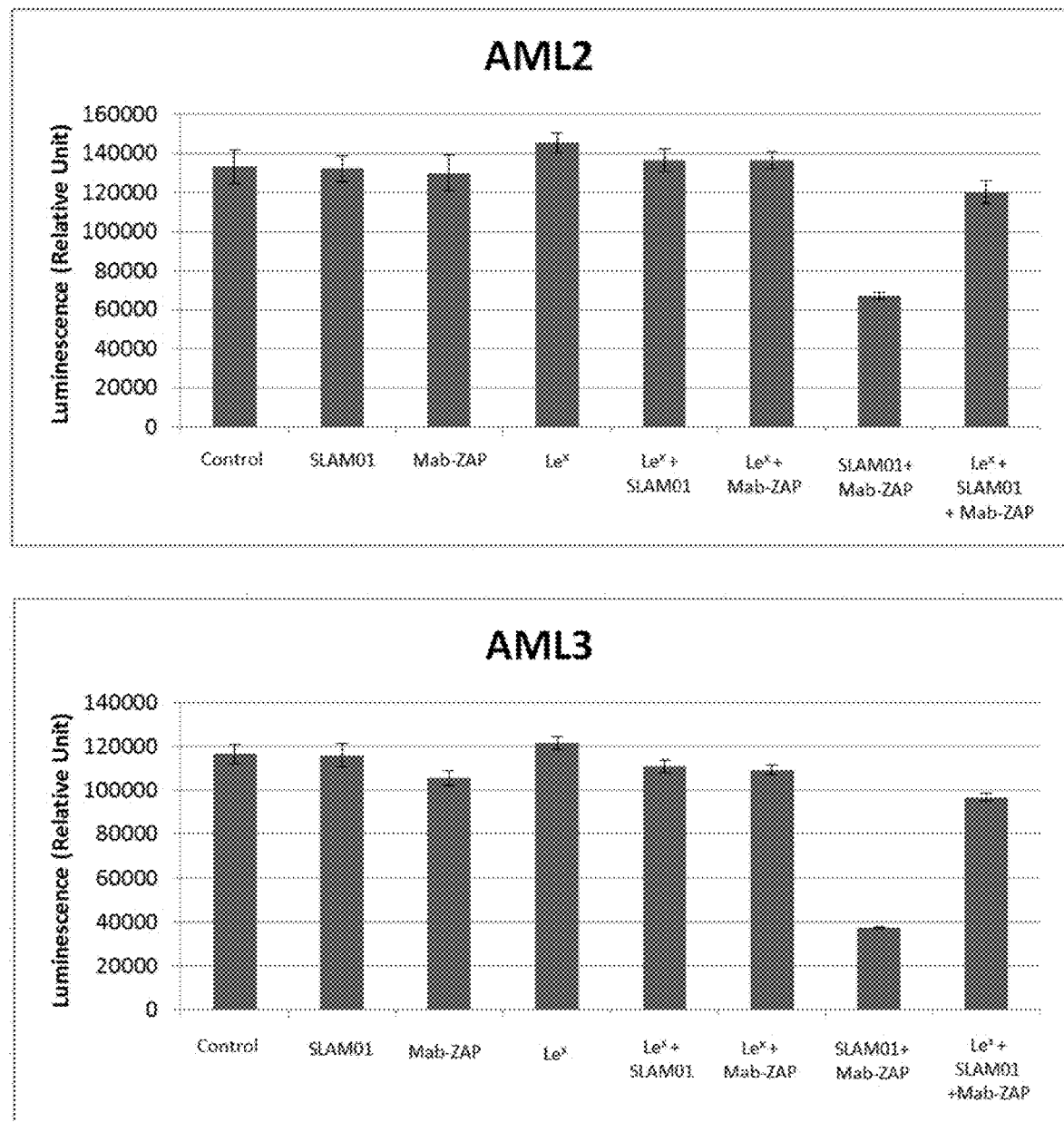
FIG. 18A shows the relative viability of AML-2 and -3 after treating with SLAM01-Mab-ZAP complex for 3 days. Both AML cell lines were treated with various conditions as shown. The addition of $Le^X$ to the SLAM01-Mab-Zap complex ($1^{st}$ column from right) rescued the cells from the cytotoxic effect of SLAM01-Mab-Zap complex ($2^{nd}$ column from right).
FIG. 18B shows Binding histograms of SLAM01 on OCI-AML3, MONO-MAC-1 and PBMC. SLAM01 was incubated on OCI-AML3, MONO-MAC-1 and peripheral blood mononuclear cells (PBMCs). SLAM01 was positive for OCI-AML3 and MONO-MAC-1, while negative for PBMC.
Figure 18:
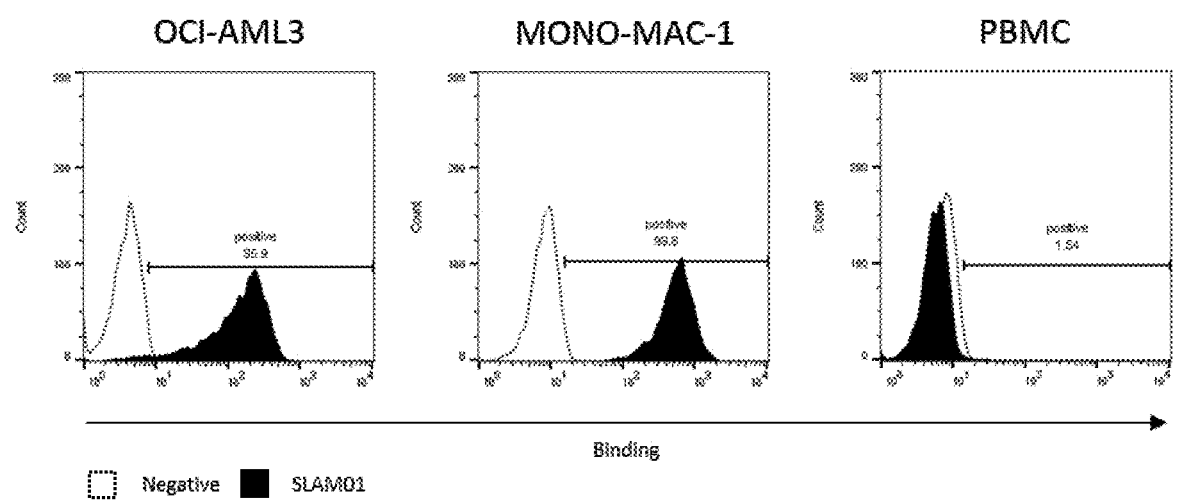

SLAM01 can potentially be used as an ADC. Flow cytometry data show some degree of internalization of SLAM01 after binding, as observed by the increase in intracellular red fluorescence when SLAM01 was conjugated to pHrodo Red (FIG. 15). SLAM01 exhibited cytotoxic activity as an ADC when indirectly conjugated to saporin via a secondary antibody on binding cancer lines in vitro (FIG. 16). Indirect conjugation of SLAM01 with the ribosome toxin, saporin (Mab-ZAP) as an ADC demonstrated killing percentage ranging from 30%-90% on the various SLAM01 positive cell lines (FIG. 17). Killing percentage was observed to be positively correlated to the binding percentage. The binding of SLAM01 to cells can be competitively inhibited by soluble free $Le^X$ (FIG. 18A). Similarly, the killing efficient of SLAM01 on target cells is reduced in the presence of $Le^X$. In addition, flow cytometry screening and agglutination assays on blood tissue samples (n=3) demonstrated no binding on PBMC, making it safe for therapeutic applications (FIG. 18B). Functionally, SLAM01, when complexed with saporin-conjugated secondary mAb, was able to internalize into and kill AML cell lines.

Example 5. Validation of Chimeric SLAM01

Figure 19:
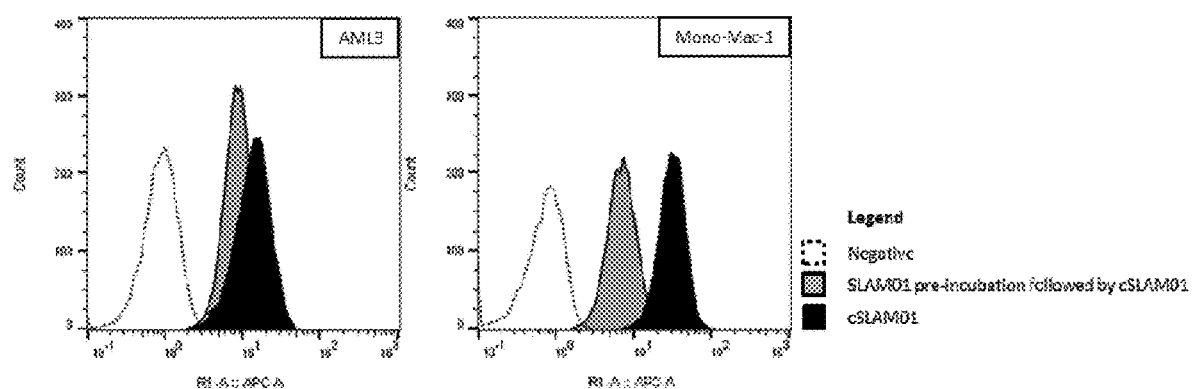
FIG. 19 shows the competitive inhibition flow cytometry of cSLAM01 and SLAM01 on AML3 and Mono-Mac-1. Competitive inhibition flow cytometry was set up between cSLAM01 and SLAM01. For the competing sample, SLAM01 was pre-incubated with the cells for 30 min at 4° C., before the addition of cSLAM01. The reduced binding histograms of cSLAM01 on the competing sample demonstrate that SLAM01 is blocking the binding of cSLAM01 to the epitope.
Figure 20:
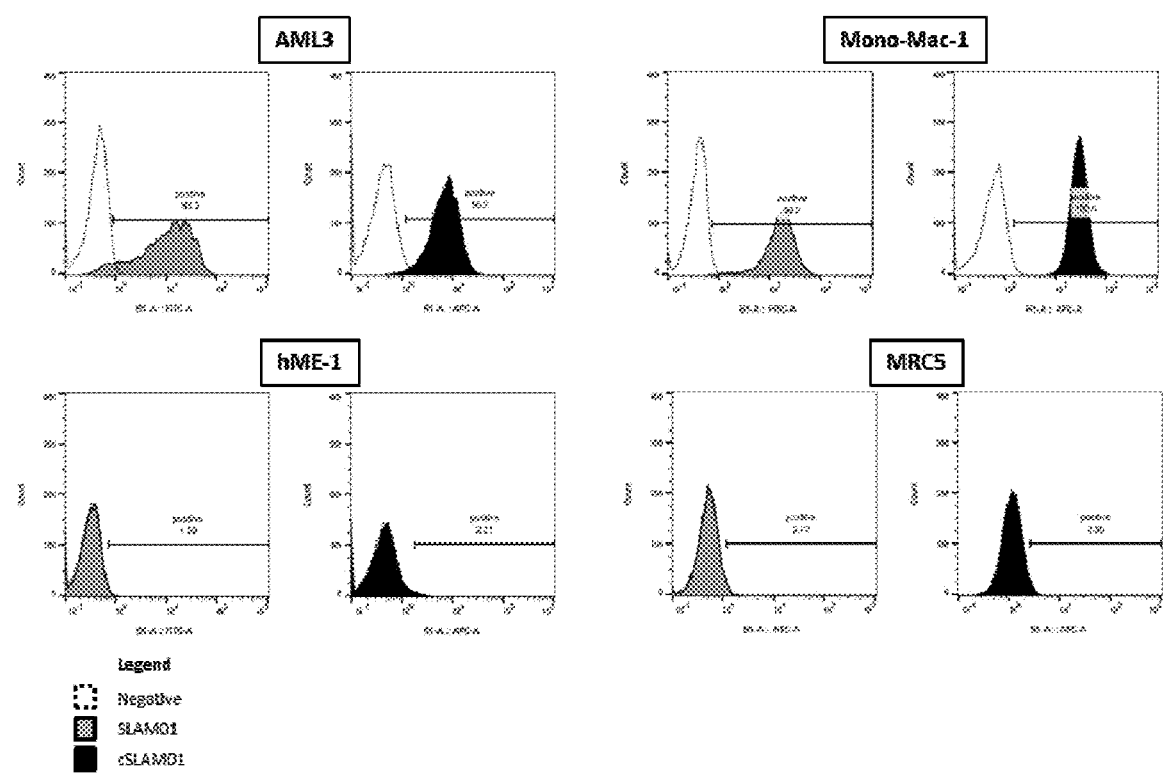
FIG. 20 shows the binding histogram of cSLAM01 and SLAM01 on AML3, Mono-Mac-1, hME-1 and MRC5. Binding profile of cSLAM01 and SLAM01 on the cell lines was compared. cSLAM01 retained binding to SLAM01-positive cell lines, and not to SLAM01-negative cell lines.

The constant region of SLAM01 was converted to that of human IgG1 to create a chimeric SLAM01 (cSLAM01). Binding of cSLAM01 to SLAM-01 positive cell lines such as AML3 and Mono-Mac-1, was confirmed in a competitive inhibition study by flow cytometry (FIG. 19). Furthermore, cSLAM01 also retained the SLAM-01 target binding profile as binding to SLAM-01 positive cell lines but not SLAM01 negative cell lines such as hME-1 and MRC5 was observed (FIG. 20). Functionally, treatment with cSLAM01 and Ig-toxin complex such as DM1, a highly potent maytansinoid, and monomethyl auristatin E (MMAE), an anti-mitotic toxin, reduced the cell viability of AML3 and Mono-Mac-1 (FIG. 21). Thus, cSLAM01 retained both the binding profile and ADC potential on SLAM-01 positive cells.

Figure 22:
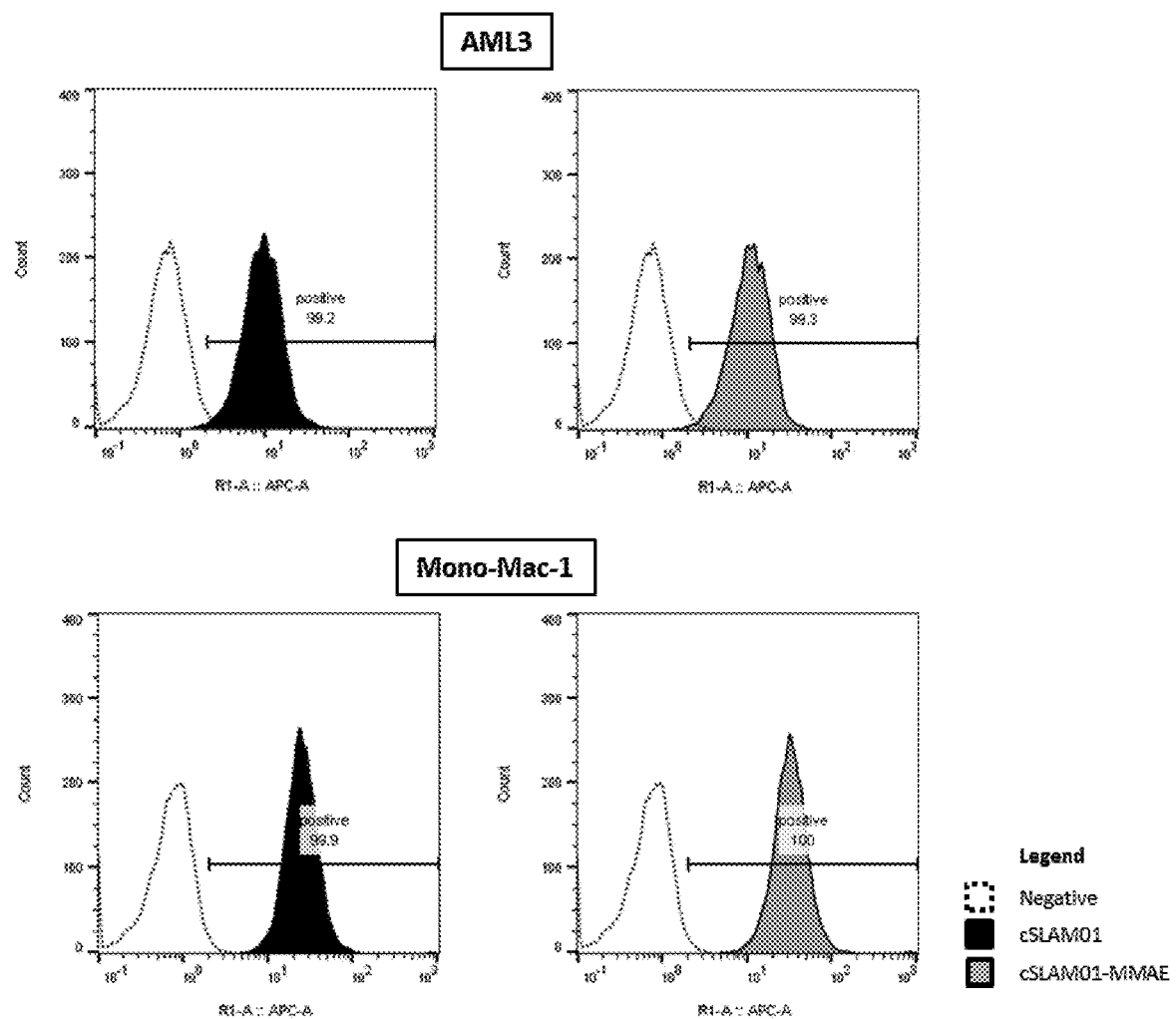
FIG. 22 shows the binding histogram of cSLAM01 and cSLAM01-MMAE on AML3 and Mono-Mac-1. Binding profile of cSLAM01-MMAE is similar to that of cSLAM01.
Figure 23:
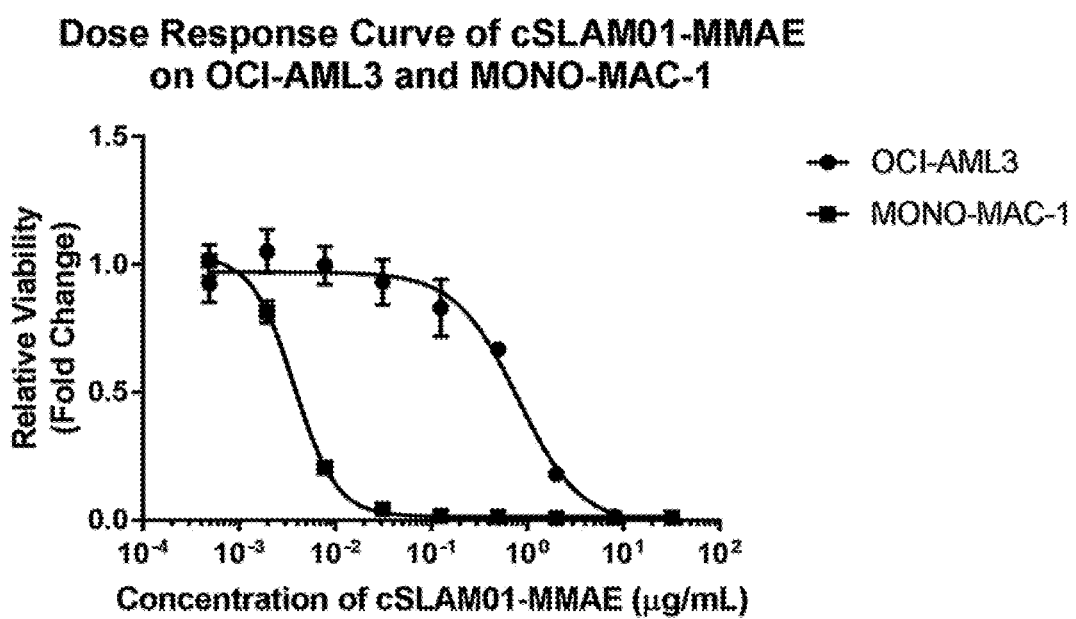
FIG. 23 shows the dose response curve of AML-3 and Mono-Mac-1 after treating with cSLAM01-MMAE for 3 days. AML3 and Mono-Mac-1 were treated with increasing dose of cSLAM01-MMAE. cSLAM01-MMAE demonstrated its ADC effect on both AML3 and Mono-Mac-1.

Following the formation and validation of cSLAM01, MMAE was directly conjugated with cSLAM01 to form cSLAM01-MMAE. Binding of cSLAM01-MMAE to both AML3 and Mono-Mac-1 was observed by flow cytometry (FIG. 22). As the binding profile of cSLAM01-MMAE is similar to cSLAM01, the ADC potential was next tested in a viability assay. Based on the dose response curve of cSLAM01-MMAE, ADC effect was observed on both AML3 and Mono-Mac-1 with a stronger potency on the latter (FIG. 23). Overall, these data highlight the potential for SLAM01 to be developed into an ADC for AML.

The invention claimed is:

1. An antigen-binding protein, or an antigen-binding fragment thereof, comprising (i) a heavy chain variable region comprising a VHCDR1 having the amino acid sequence GYTFTSYWIH (SEQ ID NO:1); a VHCDR2 having the amino acid sequence EINPSNGRTNFNEKFKN (SEQ ID NO:2) and a VHCDR3 having the amino acid sequence VDYDEAY (SEQ ID NO:3); and (ii) a light chain variable region comprising a VLCDR1 having the amino acid sequence RSSKSLLHSNGITYLY (SEQ ID NO:4), a VLCDR2 having the amino acid sequence QMSNLAS (SEQ ID NO:5), and a VLCDR3 having the amino acid sequence AQNLELWT (SEQ ID NO:6); wherein the antigen-binding protein, or the antigen-binding fragment thereof, binds to an N-linked glycan with terminal Lewis X.

2. The antigen-binding protein, or antigen-binding fragment thereof, as claimed in claim 1, wherein the heavy chain variable region comprises the amino acid sequence QVKLQQSGAELAKPGASVKLSCKASGYTFTSYWIHWVKQRPGQGLEWIGE
INPSNGRTNFNEKFKNKATLTVDKSSSTAYMQLNSLTSEDSAVYYCARVD
YDEAYWGQGTTVTVSS as set forth in SEQ ID NO: 7.

3. The antigen-binding protein, or antigen-binding fragment thereof, as claimed in claim 1, wherein the light chain variable region comprises the amino acid sequence DIVMTQAAFSNPVTLGTSASISCRSSKSLLHSNGITYLYWYLQKPGQSPQ
LLIYQMSNLASGVPDRFSSSGSGTDFTLRISRVEAEDVGVYYCAQNLELW
TFGGGTKLEIK as set forth in SEQ ID NO: 8.

4. The antigen-binding protein, or antigen-binding fragment thereof, as claimed in claim 1, wherein the antigen binding protein is selected from the group consisting of monoclonal, recombinant, polyclonal, chimeric, humanized, bispecific, and heteroconjugate antibodies; single chain Fv, a univalent antibody lacking a hinge region, a minibody, diabodies, and tandem diabodies.

5. The antigen-binding protein, or antigen-binding fragment thereof, as claimed in claim 1, conjugated to a radioisotope or a cytotoxin.

6. The antigen-binding protein, or antigen-binding fragment thereof, as claimed in claim 5, wherein the antibody is conjugated to a cytotoxin selected from the group consisting of monomethyl auristatin E (MMAE-1), mertansine (DM-1), saporin, gemcitabine, irinotecan, etoposide, vinblastine, pemetrexed, docetaxel, paclitaxel, platinum agents, vinorelbine, capecitabine, mitoxantrone, ixabepilone, eribulin, 5-fluorouracil, trifluridine and tipiracil.

7. A composition comprising a physiologically acceptable carrier and a therapeutically effective amount of the antigen-binding protein, or an antigen-binding fragment thereof, as claimed claim 1.

8. The composition as claimed in claim 7, comprising one or more further therapeutic compounds.

9. A method of treating cancer comprising administering to a subject having cancer the antigen-binding protein or the antigen-binding fragment thereof, conjugated to a radioisotope or a cytotoxin as claimed in claim 5.

10. The method of claim 9, wherein the cancer is selected from the group consisting of non-small cell lung cancer, ovarian cancer, breast cancer, acute myeloid leukemia, and colorectal cancer.

11. The method of claim 9, wherein the antigen-binding protein, or an antigen-binding fragment thereof conjugated to a radioisotope or a cytotoxin is administered with a further active pharmaceutical ingredient.

12. The method of claim 9, wherein the antigen-binding protein, or an antigen-binding fragment thereof conjugated to a radioisotope or a cytotoxin is administered with chemotherapy.

13. The method of claim 11, wherein the further pharmaceutical agent is administered separately, simultaneously, or sequentially with said antigen-binding protein, or an antigen-binding fragment thereof conjugated to a radioisotope or a cytotoxin.

14. The method of claim 12, wherein the chemotherapy is administered separately, simultaneously, or sequentially with said antigen-binding protein, or an antigen-binding fragment thereof conjugated to a radioisotope or a cytotoxin.

15. The antigen-binding protein, or antigen-binding fragment thereof, as claimed in claim 1, wherein the antigen-binding protein is a humanized monoclonal antibody.

16. The antigen-binding protein, or antigen-binding fragment thereof, as claimed in claim 1, wherein the antigen-binding protein is a chimeric monoclonal antibody.

* * * * *